US010423012B2

(12) United States Patent
Garofolo et al.

(10) Patent No.: US 10,423,012 B2
(45) Date of Patent: *Sep. 24, 2019

(54) WEARABLE VISION REDIRECTING DEVICES

(71) Applicant: Vertical Optics, LLC, San Diego, CA (US)

(72) Inventors: Timothy Richard Garofolo, Cardiff, CA (US); Scott Clear, Escondido, CA (US); Dean Loock, Encino, CA (US); Jungwoo Choi, Westlake Village, CA (US); John Michael Elam, Los Angeles, CA (US); David Lynn Devernoe, San Diego, CA (US)

(73) Assignee: Vertical Optics, LLC, San Diego, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 15/632,346

(22) Filed: Jun. 25, 2017

(65) Prior Publication Data

US 2017/0293162 A1 Oct. 12, 2017

Related U.S. Application Data

(63) Continuation of application No. 15/058,152, filed on Mar. 2, 2016, now Pat. No. 9,690,119.

(Continued)

(30) Foreign Application Priority Data

Feb. 23, 2016 (IL) .......................................... 244255

(51) Int. Cl.
*G02C 1/00* (2006.01)
*G02C 7/14* (2006.01)
*G02C 11/00* (2006.01)
*G02B 27/01* (2006.01)
*H04N 7/18* (2006.01)
*G06F 3/16* (2006.01)
(Continued)

(52) U.S. Cl.
CPC ........... *G02C 7/14* (2013.01); *G02B 27/0172* (2013.01); *G02C 7/088* (2013.01); *G02C 9/02* (2013.01); *G02C 11/10* (2013.01); *G06F 3/16* (2013.01); *G06F 3/167* (2013.01); *H04N 7/183* (2013.01); *H04N 7/185* (2013.01); *G02B 2027/0138* (2013.01); *G02B 2027/0178* (2013.01)

(58) Field of Classification Search
CPC . G02C 7/14; G02C 11/10; G02C 7/00; G02C 11/04
USPC .................... 351/158, 41, 44, 47, 57, 48, 58
See application file for complete search history.

(56) References Cited

U.S. PATENT DOCUMENTS 2,472,600 A 6/1949 Luboshez
2,862,418 A 12/1958 Herman
(Continued)

FOREIGN PATENT DOCUMENTS

CA 2568900 C 4/2011
DE 2525765 A1 12/1976
(Continued)

*Primary Examiner* — Hung X Dang

(57) ABSTRACT

The present disclosure relates to cantilevered and divergent view wearable optical systems that redirect an optical path, and provide for optimal ergonomics coupled with vision enhancement and vision magnification. Methods of use, devices, and kits are also contemplated.

20 Claims, 11 Drawing Sheets

Related U.S. Application Data

(60) Provisional application No. 62/291,129, filed on Feb. 4, 2016, provisional application No. 62/262,916, filed on Dec. 4, 2015.

(51) Int. Cl.
    *G02C 7/08* (2006.01)
    *G02C 9/02* (2006.01)

(56) References Cited

U.S. PATENT DOCUMENTS

| | | |
|---|---|---|
| 3,029,696 A | 7/1969 | Gustav |
| 3,522,983 A | 8/1970 | Daniels |
| 3,745,993 A | 7/1973 | Feinbloom |
| 4,077,703 A | 3/1978 | Pablo |
| 4,143,938 A | 3/1979 | Feinbloom |
| 4,232,943 A | 11/1980 | Rogers |
| 4,498,743 A | 2/1985 | Feinbloom |
| 4,621,283 A | 11/1986 | Feinbloom |
| 4,792,223 A | 12/1988 | Axelbaum |
| 4,797,736 A | 1/1989 | Kloots |
| 4,799,793 A | 1/1989 | Feinbloom |
| 4,902,116 A | 2/1990 | Ellis |
| 4,946,257 A | 8/1990 | Feinbloom |
| 4,988,185 A | 1/1991 | Feinbloom |
| 5,090,796 A | 2/1992 | Feinbloom |
| 5,166,823 A | 11/1992 | Feinbloom |
| 5,173,720 A | 12/1992 | Lee |
| 5,291,229 A | 3/1994 | Feinbloom |
| 5,652,636 A | 7/1997 | Feinbloom |
| 5,667,291 A | 9/1997 | Caplan |
| 5,769,523 A | 6/1998 | Feinbloom |
| 5,822,048 A | 10/1998 | Feinbloom |
| 5,838,504 A | 11/1998 | Ichikawa |
| 5,870,166 A | 2/1999 | Chang |
| 5,923,467 A | 7/1999 | Pericic |
| 6,007,035 A | 12/1999 | Feinbloom |
| 6,023,372 A | 2/2000 | Spitzer |
| 6,064,520 A | 5/2000 | Nowak |
| 6,120,145 A | 9/2000 | Lyst |
| 6,120,161 A | 9/2000 | Van Der Bel |
| 6,198,581 B1 | 3/2001 | Shoji |
| 6,280,031 B1 | 8/2001 | Zerkle |
| 6,333,814 B1 | 12/2001 | Chang |
| 6,366,411 B1 | 4/2002 | Kimura |
| 6,493,136 B2 | 12/2002 | Chang |
| 6,549,337 B2 | 4/2003 | Iizuka |
| 6,667,833 B1 | 12/2003 | Fay |
| 6,704,141 B1 | 3/2004 | Nowak |
| 7,006,861 B2 | 2/2006 | Flock |
| 7,072,124 B2 | 7/2006 | Wilt |
| 7,184,208 B2 | 2/2007 | Tamura |
| 7,212,353 B2 | 5/2007 | Sunaga |
| D592,693 S | 5/2009 | Chang |
| D602,185 S | 10/2009 | Chang |
| 7,641,335 B2 | 1/2010 | Chang |
| 7,645,050 B2 | 1/2010 | Wilt |
| 7,673,989 B2 | 3/2010 | Chang |
| 7,675,678 B2 | 3/2010 | Woker |
| D617,825 S | 6/2010 | Chang |
| 7,889,429 B2 | 2/2011 | Achtner |
| D636,011 S | 4/2011 | Chang |
| 7,980,729 B2 | 7/2011 | Feinbloom |
| 8,068,169 B2 | 11/2011 | Chang |
| 8,120,847 B2 | 2/2012 | Chang |
| 8,215,791 B2 | 7/2012 | Feinbloom |
| D682,450 S | 5/2013 | Chang |
| 8,446,670 B2 | 5/2013 | Woker |
| 8,662,709 B2 | 3/2014 | Chang |
| 8,693,732 B2 | 4/2014 | Eilat |
| 8,744,113 B1 | 6/2014 | Rickards |
| 8,749,890 B1 | 7/2014 | Wood |
| 8,814,691 B2 | 8/2014 | Haddick |
| 8,830,588 B1 | 9/2014 | Brown |
| 8,851,709 B2 | 10/2014 | Feinbloom |
| 8,964,291 B2 | 2/2015 | Chang |
| 9,052,455 B2 | 6/2015 | Chang |
| 9,053,483 B2 | 6/2015 | Geisner |
| 9,122,916 B2 | 9/2015 | Fujimura |
| 9,132,346 B2 | 9/2015 | Huebner |
| 9,142,062 B2 | 9/2015 | Maciocci |
| 9,189,021 B2 | 11/2015 | Jerauld |
| D746,354 S | 12/2015 | Chang |
| 9,202,443 B2 | 12/2015 | Perez |
| 9,208,615 B2 | 12/2015 | Kashitani |
| 9,219,849 B2 | 12/2015 | Feinbloom |
| 9,250,746 B2 | 2/2016 | Wala |
| 9,305,365 B2 | 4/2016 | Lovberg |
| 9,384,594 B2 | 7/2016 | Maciocci |
| 9,690,119 B2 * | 6/2017 | Garofolo ............... G02C 7/14 |
| 2006/0245052 A1 | 11/2006 | Wilt |
| 2007/0171520 A1 | 7/2007 | Fante |
| 2007/0273983 A1 | 11/2007 | Hebert |
| 2008/0169998 A1 | 7/2008 | Jacobsen |
| 2009/0116225 A1 | 5/2009 | Feinbloom |
| 2010/0079356 A1 | 4/2010 | Hoellwarth |
| 2010/0110368 A1 | 5/2010 | Chaum |
| 2010/0149323 A1 | 6/2010 | Yoo |
| 2010/0165605 A1 | 7/2010 | Feinbloom |
| 2010/0165617 A1 | 7/2010 | Feinbloom |
| 2010/0199232 A1 | 8/2010 | Mistry |
| 2010/0290115 A1 | 11/2010 | Chang |
| 2011/0227813 A1 | 9/2011 | Haddick |
| 2012/0119978 A1 | 5/2012 | Border |
| 2012/0120636 A1 | 5/2012 | Wilt |
| 2012/0235887 A1 | 9/2012 | Border |
| 2012/0249591 A1 | 10/2012 | Maciocci |
| 2012/0275140 A1 | 11/2012 | Feinbloom |
| 2013/0010068 A1 | 1/2013 | Tiernan |
| 2013/0044042 A1 | 2/2013 | Olsson |
| 2013/0094081 A1 | 4/2013 | Chang |
| 2013/0147859 A1 | 6/2013 | Kobayashi |
| 2013/0169683 A1 | 7/2013 | Perez |
| 2013/0222757 A1 | 8/2013 | Klein |
| 2013/0235331 A1 | 9/2013 | Heinrich |
| 2013/0249787 A1 | 9/2013 | Morimoto |
| 2013/0293583 A1 | 11/2013 | Kashitani |
| 2013/0328770 A1 | 12/2013 | Parham |
| 2014/0028968 A1 | 1/2014 | Olsson |
| 2014/0036356 A1 | 2/2014 | Feinbloom |
| 2014/0132484 A1 | 5/2014 | Pandey |
| 2014/0139420 A1 | 5/2014 | Wu |
| 2014/0184881 A1 | 7/2014 | McKinley |
| 2014/0184890 A1 | 7/2014 | McKinley |
| 2014/0184899 A1 | 7/2014 | McKinley |
| 2014/0198190 A1 | 7/2014 | Okumu |
| 2014/0270685 A1 | 9/2014 | McLean |
| 2014/0293588 A1 | 10/2014 | Chang |
| 2015/0002676 A1 | 1/2015 | Yoo |
| 2015/0002768 A1 | 1/2015 | Wu |
| 2015/0003049 A1 | 1/2015 | Chang |
| 2015/0022542 A1 | 1/2015 | Baba |
| 2015/0048911 A1 | 2/2015 | Dauer |
| 2015/0084841 A1 | 3/2015 | Hilkes |
| 2015/0146090 A1 | 5/2015 | Feinbloom |
| 2015/0146091 A1 | 5/2015 | Feinbloom |
| 2015/0146290 A1 | 5/2015 | Chang |
| 2015/0169050 A1 | 6/2015 | Publicover |
| 2015/0309316 A1 | 10/2015 | Osterhout |
| 2015/0310668 A1 | 10/2015 | Ellerbrock |
| 2015/0331230 A1 | 11/2015 | Wilt |
| 2015/0377462 A1 | 12/2015 | Wilt |
| 2016/0026067 A1 | 1/2016 | Feinbloom |

FOREIGN PATENT DOCUMENTS

| | | |
|---|---|---|
| DE | 202011005311 U1 | 11/2011 |
| EP | 1491938 B1 | 1/2010 |
| EP | 2440845 A1 | 4/2012 |
| GB | 2332062 A | 6/1999 |
| JP | 4741813 B2 | 8/2011 |
| WO | 199637730 A1 | 11/1996 |
| WO | 199954773 A1 | 10/1999 |
| WO | 2003007048 A2 | 1/2003 |

(56) References Cited

FOREIGN PATENT DOCUMENTS

| WO | 2010115082 A1 | 10/2010 |
| WO | 2010144426 A1 | 12/2010 |
| WO | 2012018784 A1 | 2/2012 |
| WO | 2013049248 A2 | 4/2013 |
| WO | 2013177654 A1 | 12/2013 |
| WO | 2014053841 A2 | 4/2014 |
| WO | 2014210091 A1 | 12/2014 |
| WO | 2015048911 A1 | 4/2015 |
| WO | 2015095737 A2 | 6/2015 |

\* cited by examiner

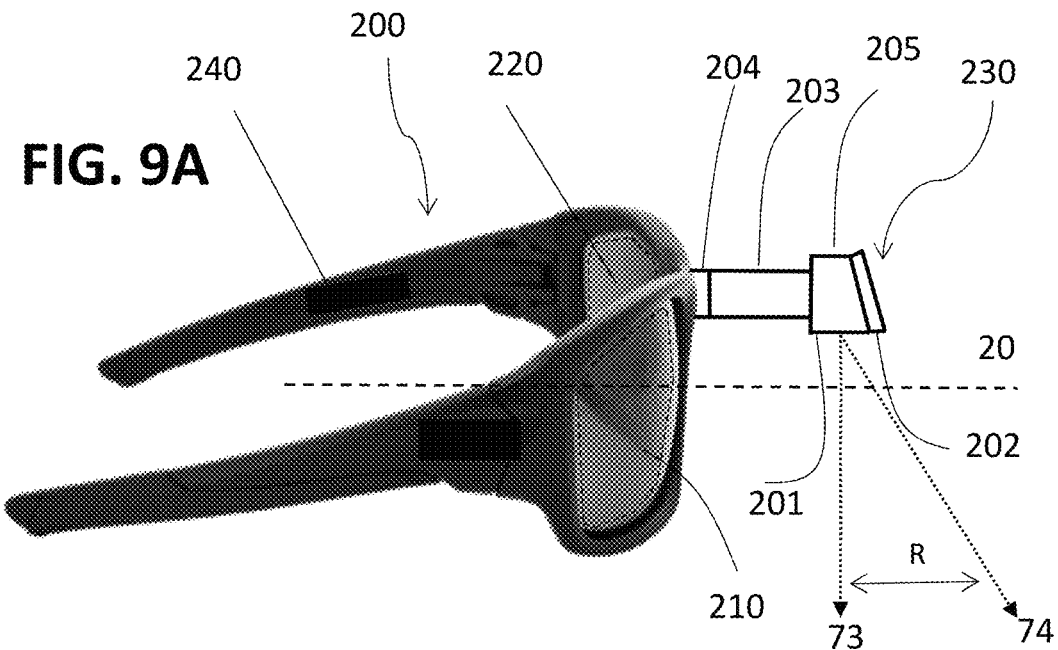
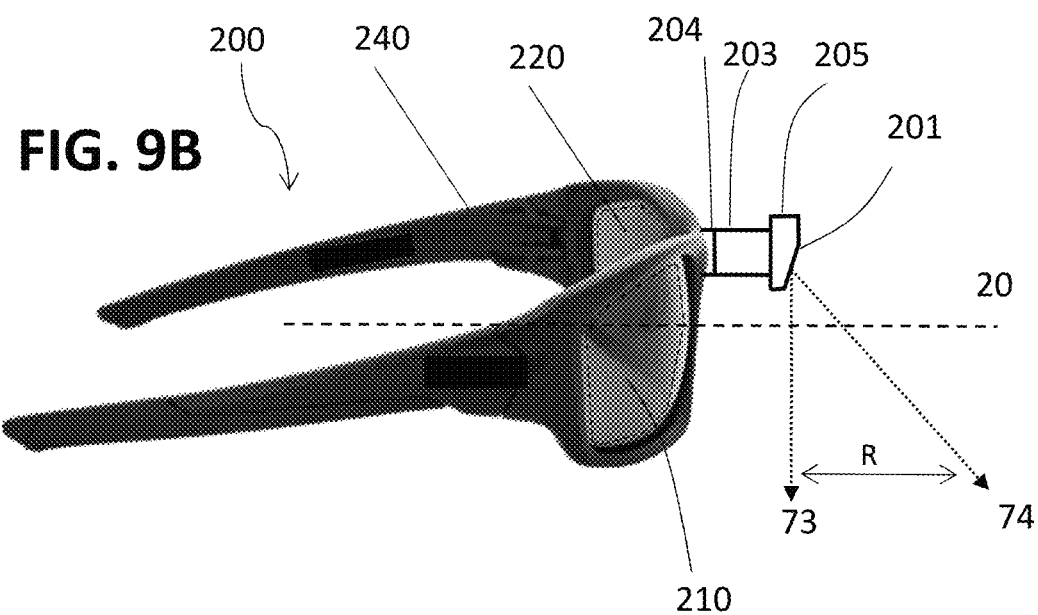

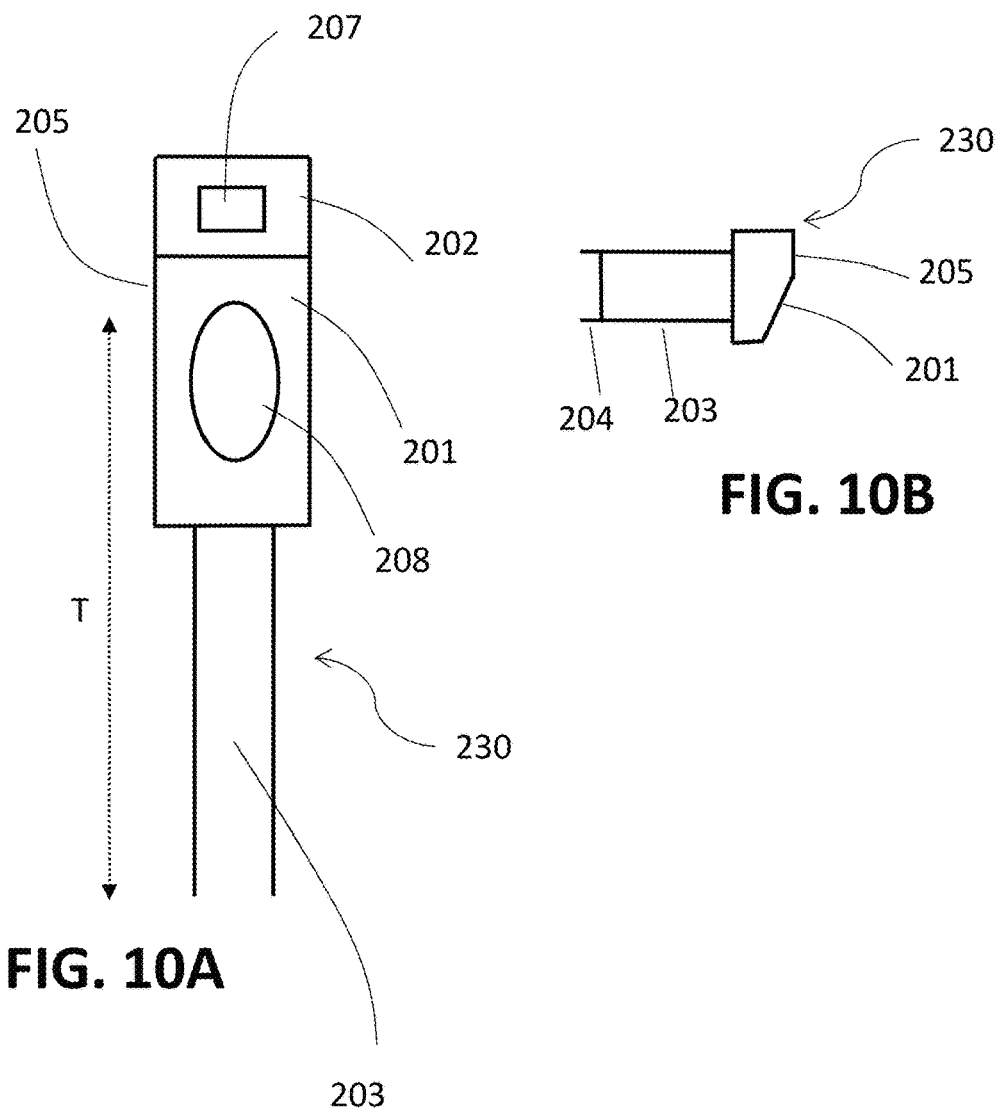

WEARABLE VISION REDIRECTING DEVICES

RELATED APPLICATIONS

This application claims is a continuation application of U.S. patent application Ser. No. 15/058,152, filed Jun. 17, 2017, now U.S. Pat. No. 9,690,119, which claims priority to Israel Patent Application No. 244255, filed Feb. 23, 2016; U.S. Provisional Patent Application No. 62/291,129, filed Feb. 4, 2016; U.S. Provisional Patent Application No. 62/262,916, filed Dec. 4, 2015; and U.S. Provisional Patent Application No. 62/162,611, filed May 15, 2015, the contents of each of which are hereby incorporated by reference in their entirety.

TECHNICAL FIELD

The present disclosure relates to wearable optical devices that redirect the vision of a user.

BACKGROUND

A loupe is a known magnification device that, unlike a conventional magnifying glass, is typically devoid of a handle and, therefore, requires the lens body to be supported or otherwise grasped by, for example, the user's hand. However, for professionals such as surgeons, dentists, vets and jewelers, this can be problematic, since both hands are typically required when working.

Loupes are widely used for magnifying a work area during precision work such as surgery, dental work, electronics work, and assembly of miniature parts. Typically, a pair of loupes are provided that may be mounted to an eyeglass frame or headband. Loupes combine the long working distance of the telescope with the high quality magnification of a microscope. This type of optical instrument provides the user with a magnified field of view at a predetermined distance. The mounting assemblies used in typical loupes provide a variety of degrees of freedom for the user, for example, by way of adjusting interpupillary distance and arranging the eyeglass frame in a specific orientation on the user's head. Although a wide range of adjustments increases flexibility, manipulation of the user's body outside of an optimal ergonomic orientation is generally required. For example, a user such as a dentist is required to bend at the lower and upper back, and neck, to provide an optimal viewing angle for a procedure. In addition, other medical and industrial professionals, in addition to laymen performing recreational and/or routine tasks often have to assume a back or neck contorted posture to assume an optimal viewing angle of something or some task. Such postures cause strain in the head, neck, and other areas leading to accelerated fatigue and overuse injuries, especially if such a posture is required for prolonged periods of time.

As such, there exists a need in the art to provide ergonomically-optimal high quality magnification for users performing precision work or other tasks. The present disclosure addresses these and other needs in the art.

SUMMARY

In frequent embodiments, a wearable optical device or system is provided, comprising: a user wearable frame; a centered display supported by the frame; and a cantilevered imaging modality supported by the frame in data connection with the display. Generally, the display is positioned for viewing by the user in a horizontal optical path. The term "cantilevered," among others, is defined herein.

Also, in frequent embodiments, a wearable optical device or system is provided, comprising: a user wearable frame; a centered display supported by the frame; and a divergent view imaging modality supported by the frame and in data connection with the display. Generally, the display is positioned for viewing by the user in a horizontal optical path. The term "divergent," among others, is defined herein.

Also, in frequent embodiments, a wearable optical device or system is provided, comprising: a user wearable frame; a display supported by the frame; and a cantilevered divergent view imaging modality supported by the frame and in data connection with the display. The terms "cantilevered" and "divergent," among others, are defined herein. Generally, the display is positioned for viewing by the user in a horizontal optical path.

In frequent embodiments, a wearable optical device or system is provided, comprising: a user wearable frame comprising a centered viewing portion that is viewable by a user via a horizontal optical path; and a vision redirecting mechanism defining a work area optical path in optical communication with the viewing portion, the horizontal optical path and the work area optical path being different optical paths, wherein the vision redirecting mechanism or the viewing portion magnifies an image passed through the work area optical path. Frequently, the viewing portion comprises a display.

Also, in frequent embodiments, a wearable optical device or system is provided, comprising: a user wearable frame comprising a viewing portion defining a horizontal optical path for the user; and a vision redirecting mechanism that redirects the horizontal optical path to a second optical path defined by a different angle versus the horizontal optical path, wherein the vision redirecting mechanism magnifies an image passed through the second optical path and the horizontal optical path.

Often, the viewing portion is comprised in a lens supported by the frame. Also often, the user wearable frame is adapted to be worn on the head of a user.

In frequent embodiments, the vision redirecting mechanism is cantilevered or comprised in or attached to an imaging extension. Such a vision directing mechanism is frequently a camera. The term "cantilevered," among others, is defined herein.

Often, optical communication comprises data transmission of an image obtained by a camera comprised in the vision redirecting mechanism to the viewing portion.

In frequent embodiments, the viewing portion comprises a display. Often, the display comprises an inner surface and an outer surface and the outer surface comprises smart glass. In frequent embodiments, the display comprises smart glass. The smart glass often comprises a smart glass technology selected from electrochromic smart glass, photochromic smart glass, suspended particle smart glass, liquid crystal smart glass, or nano smart glass.

The vision redirecting mechanism or display is frequently in data communication with a database and an imaging software. Often, the data communication or data connection is a wireless data connection, frequently selected from the group consisting of WPAN/Bluetooth, Coexistence, High Rate WPAN, Low Rate WPAN, mesh Networking, Body Area Networks, WiFi, WiMax, RFID, and/or Visible Light Communication.

The work area optical path is, in the most frequent embodiments, oriented downward at an angle relative to the horizontal optical path. Often, the angle is between 45° to 90°. Also often, the angle is between 30° to 100°. In certain embodiments, the angle is between 45° to 120°. In certain embodiments, the angle is between 60° to 120°. In certain embodiments, the angle is between 60° to 80°. In certain embodiments, the angle is between 45° to 85°. In certain embodiments, the angle is between 50° to 90°. In certain embodiments, the angle is between 60° to 90°. In certain embodiments, the angle is between 70° to 90°. In certain embodiments, the angle is between 80° to 90°. In certain embodiments, the angle is between 46° to 75°. In certain embodiments, the angle is between 47° to 88°. In certain embodiments, the angle is between 55° to 78°.

In frequent embodiments, the imaging magnification comprises between about 1.0× to 5.0× magnification of the image. The imaging magnification often comprises between about 1.0× to 10.0× magnification of the image. The imaging magnification also often comprises between about 10.0× to 400.0× magnification of the image. The imaging magnification also often comprises between about 3.0× to 400.0× magnification of the image. In certain embodiments, the imaging magnification comprises between about 3.0× to 5.0× magnification of the image. In certain embodiments, the imaging magnification comprises between about 4.0× to 8.0× magnification of the image. In certain embodiments, the imaging magnification comprises between about 5.0× to 15.0× magnification of the image. In certain embodiments, the imaging magnification comprises between about 10.0× to 40.0× magnification of the image. In certain embodiments, the imaging magnification comprises between about 5.0× to 30.0× magnification of the image. In certain embodiments, the imaging magnification comprises between about 3.0× to 30.0× magnification of the image. In certain embodiments, the imaging magnification comprises between about 5.0× to 20.0× magnification of the image. In certain embodiments, the imaging magnification comprises between about 2.0× to 10.0× magnification of the image.

In certain embodiments, the optical communication comprises direct image transmission across the work area optical path and horizontal optical path. Often, the work area optical path is oriented downward at an angle relative to the horizontal optical path. The downward at an angle relative to the horizontal optical path is often between 45° to 90°. This angle is also often between 30° to 100°. In certain embodiments, the angle is between 45° to 120°. In certain embodiments, the angle is between 60° to 120°. In certain embodiments, the angle is between 60° to 80°. In certain embodiments, the angle is between 45° to 85°. In certain embodiments, the angle is between 50° to 90°. In certain embodiments, the angle is between 60° to 90°. In certain embodiments, the angle is between 70° to 90°. In certain embodiments, the angle is between 80° to 90°. In certain embodiments, the angle is between 46° to 75°. In certain embodiments, the angle is between 47° to 88°. In certain embodiments, the angle is between 55° to 78°. Often, the frame comprises an eyeglass frame. The display is often comprised in an eyeglass lens positioned in the frame.

Most frequently, the system further comprising a light source. Often, the light source emits a light signal that is coextensive with an optical path of the imaging modality.

Also frequently, the imaging modality is oriented downward relative to the frame. Often, the imaging modality is oriented between about 45° to about 90° below horizontal. In certain embodiments, the angle is between 45° to 120° below horizontal. In certain embodiments, the angle is between 60° to 120° below horizontal. In certain embodiments, the angle is between 60° to 80° below horizontal. In certain embodiments, the angle is between 45° to 85° below horizontal. In certain embodiments, the angle is between 50° to 90° below horizontal. In certain embodiments, the angle is between 60° to 90° below horizontal. In certain embodiments, the angle is between 70° to 90° below horizontal. In certain embodiments, the angle is between 80° to 90° below horizontal. In certain embodiments, the angle is between 46° to 75° below horizontal. In certain embodiments, the angle is between 47° to 88° below horizontal. In certain embodiments, the angle is between 55° to 78° below horizontal. Most frequently, "horizontal" refers to a "horizontal optical path" as that phrase is defined herein.

Often, the imaging modality or vision redirecting mechanism comprises a camera. In certain embodiments, the camera comprises a 180° HD camera. In certain embodiments, the camera comprises a 360° HD camera. Often, imaging modality communicates between about 1.0× to 5.0× magnification of a work area to the display. Also often, the imaging modality communicates between about 1.0× to 10.0× magnification of a work area to the display. In certain embodiments, the imaging modality communicates between about 10.0× to 400.0× magnification of a work area to the display. In certain embodiments, the imaging modality communicates between about 5.0× to 40.0× magnification of a work area to the display. In certain embodiments, the imaging modality communicates between about 5.0× to 30.0× magnification of a work area to the display. In certain embodiments, the imaging modality communicates between about 5.0× to 20.0× magnification of a work area to the display. In certain embodiments, the imaging modality communicates between about 3.0× to 10.0× magnification of a work area to the display. Optical zoom and/or digital zoom technology is often used to provide magnification.

The system is often comprised in a dental operatory system. In frequent embodiments, the device is in data communication with imaging software or medical apparatus. Often, the device is in wireless data communication (e.g., WPAN/Bluetooth, Coexistence, High Rate WPAN, Low Rate WPAN, mesh Networking, Body Area Networks, WiFi, WiMax, RFID, other wireless networks, Visible Light Communication, etc.) with imaging software, a laboratory information system, a medical apparatus, and/or an insurance efiling system. The medical apparatus is often any medical apparatus capable of or adaptable to be in data communication (wired or wireless) with the devices or systems contemplated herein. In certain embodiments, the medical apparatus comprises a dental crown milling machine, or inlay, only, crown, or veneer machine.

The imaging modality, display, and/or viewing portion is/are often voice-controlled. Voice control often controls data import and data export. In certain embodiments, the voice control is provided in a manner that permits the user to perform voice-to-text commands or operations. Often, a microphone is provided in the system or device to assist with voice control and such a microphone is positionable or positioned in close proximity to the mouth of the user while the system is worn by the user and in operation.

In frequent embodiments, the display and/or viewing portion comprises inner and outer portions, and the outer portion comprises a smart glass shading technology ("smart glass technology" is often referred to herein as smart glass for simplicity). Often, the smart glass shading technology is controlled by voice-command or remote actuation by the user. Often, the smart glass technology comprises electrochromic smart glass, photochromic smart glass, suspended particle smart glass, liquid crystal smart glass, or nano smart glass technology.

In frequent embodiments, the imaging modality, display, and/or viewing portion is/are remote controlled by the user. Often, the remote control is comprised in a user hand-held tool or device. In certain embodiments, the remote control is positioned in a dental mirror. In certain embodiments, the remote control is positioned on the body of the user or in another location where the remote control can be controlled by the user or another person. In certain embodiments, system or device controls are positioned on the system or device, for example, on the frame or housing of the system or device. In certain embodiments, a touchpad is provided on the system or device for operation of system or device controls.

In frequent embodiments, the device is used as equivalent to an intraoral camera or extraoral camera for medical or insurance purposes. Often, the display is adapted to provide an image of a written communication from a remote location. Also often, the display is adapted to provide an image from a device or camera positioned remotely to the device. In frequent embodiments, the device is connected with a remote database for accessing or storing images.

In certain frequent embodiments, a dental system is provided comprising a wearable optical device described herein claim in data communication with a storage database and imaging software.

In certain embodiments, a tracking algorithm, software, or firmware is included with the system. Also, in certain embodiments, the imaging modality is adapted to provide visual tracking to focus on a work area in an automated manner. Often, in such embodiments, the tracking comprises identification of a feature of a work area or identifier such as a fiducial or other marker to identify a portion or a boundary of a work area.

Often, the work area is a mouth or surgical site of a subject.

Kits comprising a wearable optical system described herein are also frequently provided comprising the components described herein.

Methods of using wearable optical devices described herein are also frequently provided. In frequent embodiments, the methods involve improving the posture or ergonomic positioning of the user. Devices described herein are directed toward, inter alia, improving the ergonomic environment of the user.

In frequent embodiments, a method of improving workflow in a dental office is provided, comprising: donning a system by a user, the system comprising a user wearable frame comprising a centered viewing portion that is viewable by a user via a horizontal optical path; and a vision redirecting mechanism defining a work area optical path in optical communication with the viewing portion, the horizontal optical path and the work area optical path being different optical paths, wherein the vision redirecting mechanism or the viewing portion magnifies an image passed through the work area optical path; imaging a work area with the system; and transmitting data comprising or related to the image to a remote location; or sending or receiving data related to the workflow of the dental office from or to the user. Often, the data transmission, sending data, or receiving data is performed using a wireless data connection. Such wireless data connection is often selected from the group consisting of WPAN/Bluetooth, Coexistence, High Rate WPAN, Low Rate WPAN, mesh Networking, Body Area Networks, WiFi, WiMax, and Visible Light Communication.

In frequent embodiments, an optical device is provided, comprising: a support operable for positioning on the head of a subject; and a magnifying portion mounted on the support having an optical path defined by a first path and a second path, wherein an angle of the first path of the optical path differs from an angle of the second path of the optical path relative to a horizontal orientation. The "angle" often is within 45° to 100°, though additional angles and angle ranges are explicitly contemplated herein. The horizontal orientation often refers to a horizontal optical path.

In frequent embodiments, a vision redirecting device is provided, comprising a magnifying portion having an optical path defined by a first path and a second path, wherein an angle of the first path of the optical path differs from an angle of the second path of the optical path relative to a horizontal orientation, wherein the magnifying portion is positioned in a housing, and the housing is adapted to attach to an optical loupe. The "angle" often is within 45° to 100°, though additional angles and angle ranges are explicitly contemplated herein. The horizontal orientation often refers to a horizontal optical path.

Also, in frequent embodiments a wearable vision redirecting device is provided, comprising a housing defining an optical path having a first path contiguous with a second path and an intersection defining an angled connection of the first path with the second path, wherein the angle is between about 20 degrees to about 90 degrees.

Often, the magnifying portion is positioned in a housing. Also often, the magnifying portion, device, or housing comprises at least one of a lens, a mirror, or a prism such as a roof prism or diagonal. The prism is often a pentaprism. In certain embodiments, an electronic vision mechanism comprising a projector, display (e.g., an LCD display or screen), or camera is comprised in the housing. In certain embodiments, the housing is movably adjustable relative to the support. Often, the housing is vertically adjustable.

In frequent embodiments, the support comprises an eyeglass frame, face mask, helmet, a headband and visor device, or apparatus otherwise adapted to be worn on the head of a user, or an apparatus adapted to be worn within the line of vision of a user. Often, the device further includes a light source such as an LED light source, a tungsten halogen light, a plasma arc curing light, and/or a laser. Often the light source is attached to the support or the housing. Often, the light source emits a light signal that is coextensive with the first or second path of the optical path. Also often, the light source emits a light signal in the visible spectrum, though dental curing lights, ultraviolet, and laser lights are also often incorporated in certain embodiments. In general, the light source is incorporated in a manner that reduces or eliminates shadowing on a work area or at the end of the focal length.

Frequently, the optical path defines a focal length.

In frequent embodiments, the angle of the first path of the optical path is parallel with the horizontal orientation. Often, the angle of the second path of the optical path is at about a 15 degree to about a 90 degree vertical variance from the horizontal orientation. The horizontal orientation often refers to a horizontal optical path. Also often, the angle of the second path of the optical path is at about a 1 degree to about a 90 degree vertical variance from the horizontal orientation. Often, the angle of the second path of the optical path is at about a 15 degree, to about a 45 degree, vertical variance from the horizontal orientation. Frequently, the angle of the second path of the optical path is at about a 15 degree, to about an 80 degree, vertical variance from the horizontal orientation. In frequent embodiments, the angle is between about 60 degrees to about 80 degrees. Often, wherein the angle is between about 45 degrees to about 70 degrees.

In certain embodiments, the angle of the second path of the optical path is adjustably variable relative to the angle of the first path of the optical path.

In frequent embodiments, device or vision redirecting device is an add-on optical device.

Also, in frequent embodiments, the magnifying portion imparts a magnification along the focal length of between about 0.5× to about 10.0× versus sight without magnification. Often, the magnification portion imparts a magnification along the focal length of between about 2.0× to about 5.0× versus sight without magnification. Also often, the optical path defines a focal length that is between about 1.1× to about 2.5× longer than the focal length of the optical loupe.

Also frequently, a wearable vision redirecting device is provided, comprising: a head attachment portion; a magnifying portion; and a vision redirecting mechanism, wherein the vision redirecting mechanism redirects light travelling from a first direction to exit the vision redirecting mechanism travelling in a second direction that is different from the first direction, wherein the light travelling in the first or second directions passes through the magnifying portion. Often, the second direction is toward an eye of a user wearing the wearable vision redirecting device, and the first direction is a straight line from a work area. The first and second directions (including first and second paths, light paths, or optical paths) are generally intended herein as distinct and different compared with a focused light signal where the general direction of the light is maintained, while the signal is concentrated, for example by passage through a lens.

Also often, the magnifying portion is positioned within the first direction or the second direction such that an image embodied in the light is magnified.

Frequently, an angle of the vision redirecting mechanism is adjustable such that the second direction is maintained while the first direction is changed according to an adjustment of the angle. Often, a position of the magnifying portion or the vision redirecting mechanism is adjustable relative to the head attachment portion.

Also frequently, the magnifying portion and the vision redirecting mechanism are positioned in a housing.

Most frequently, the head attachment portion is adapted to be positioned on a head of a user. Often, wherein the head attachment portion comprises a headband.

Also frequently, the devices described herein further comprise a light source for illuminating a work area. Often, the light source emits a light signal that is coextensive with the first or second direction of the light (e.g., optical path). Also often, the light source emits a light signal in the visible spectrum, though dental curing lights, ultraviolet, and laser lights are also often incorporated in certain embodiments.

Often, the device further comprises a power source. Often, the power source comprises a battery. Less frequently, the power source is connected using an external cord. Often, the power source comprises a removable battery. Frequently, the power source is positioned on the head attachment portion. Also frequently, the power source is rechargeable. Often, the power source is operated using a switch positioned on the device. Also often, the switch is a capacitive sensor.

In frequent embodiments, the head attachment portion is adjustable to be tightened or loosened. Tightening and loosening is provided to adapt the head attachment portion to fit a specific user of the device to that it may be worn by the user in a securely attached manner.

Frequently, the device comprises a front shield. Often, the magnifying portion is positioned in contact with the front shield.

In frequent embodiments, the device comprises an electronic vision mechanism. In certain embodiments, an electronic vision mechanism comprising a projector, display (e.g., an LCD display or screen), and/or a camera is provided in the device. Often, the electronic vision mechanism is comprised in a housing. In certain embodiments, the electronic vision mechanism is comprised in the visor portion. A screen such as an LCD screen or projector screen may often be provided adjacent to, as part of, or forming, a front shield.

Also in frequent embodiments, the device comprises a protective shield or a protective coating on a shield, or other portion of the device, lying within a light path between the user and the work area.

The device or system often comprises a speaker (e.g., in an ear-piece) and/or a microphone for reception and transmission of an auditory information such as a communication or a signal. Often, the communication or signal cues the device or system to display or transmit an image. Also often, the communication or signal cues another device to begin, modify, or cease operation, or to do something in particular such as transmit data. The other device is often a remote device, for example a remote device within or remote from a dental or surgical operatory or a work area. As used herein, the term "data" encompasses auditory information.

The device or system is often utilized in the jewelry trade, geology, gemology, watchmaking, photography, laboratory technicians, collectors, printing, dentistry, surgery, biology, chemistry, education, meteoritics, electronics, manufacturing, fabrication, tattooing, ophthalmology, dermatology, reading, drone operation, writing, law enforcement or military, home images or videography, and/or professional videography.

In certain limited electronic vision embodiments, the device comprises a display and optionally includes a camera connected to the device.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

FIG. 9A depicts a side view of an exemplary vision re-directing device.

FIG. 9B depicts a side view of another exemplary vision re-directing device.

FIG. 10A depicts a plan view of the bottom, looking up, of the electronic vision modality of the device of FIG. 9A.

FIG. 10B depicts a side view of another exemplary electronic vision modality.

FIG. 10C depicts a side view of another exemplary electronic vision modality.

DETAILED DESCRIPTION

Figure 1:
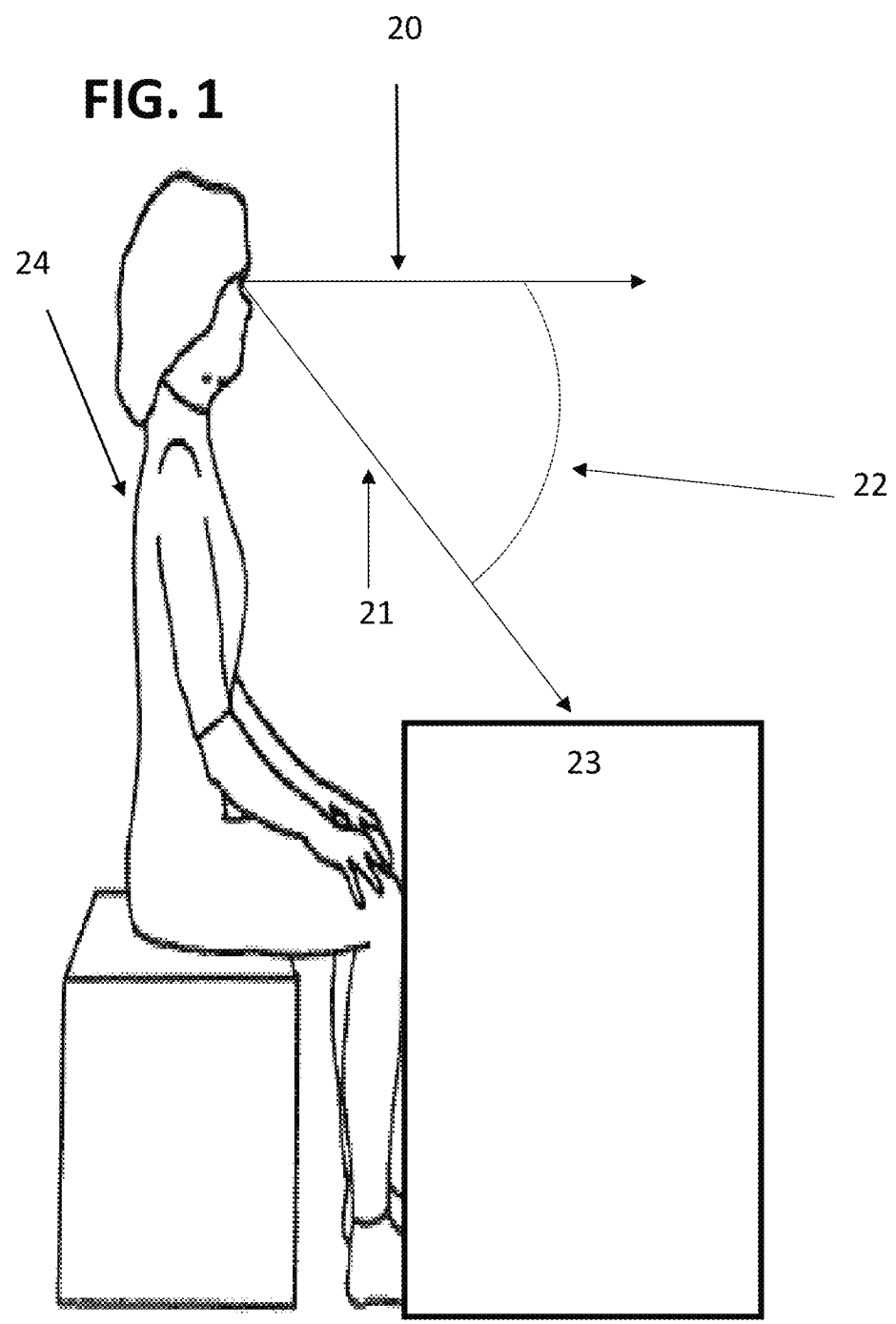
FIG. 1 depicts a seated person and an exemplary optical path alteration.

The features of the presently disclosed solution may be economically molded or assembled by using one or more distinct parts and associated components which, may be assembled together for removable or integral application.

Unless defined otherwise, all technical and scientific terms used herein have the same meaning as is commonly understood by one of ordinary skill in the art to which this disclosure belongs. In some cases, terms with commonly understood meanings are defined herein for clarity and/or for ready reference, and the inclusion of such definitions herein should not necessarily be construed to represent a substantial difference over what is generally understood in the art. If a definition set forth in this section is contrary to or otherwise inconsistent with a definition set forth in the patents, application, published applications and other publications that are herein incorporated by reference, the definition set forth in this section prevails over the definition that is incorporated herein by reference.

All patents, applications, published applications and other publications referred to herein are incorporated by reference in their entirety, or the specific reason for which they are cited.

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

The use of the term "embodiment" means that a particular feature, structure, or characteristic described in connection with the embodiment is included in at least one embodiment of described subject matter. As such, the appearance of the phrases "in one embodiment" or "in an embodiment" throughout the present disclosure is not necessarily referring to the same embodiment. Furthermore, the particular features, structures, or characteristics may be combined in any suitable manner in one or more embodiments.

As used herein, "user" refers to an animal, including, but not limited to, a primate (e.g., human). Generally, a "user" refers to a person wearing or operating a system or device described herein.

As used herein, "work area" refers to an area, object, or thing to be viewed by a user, or a portion thereof; most frequently using the devices of the present disclosure. In frequent embodiments, the work area comprises a mouth or surgical site of a subject.

As used herein, "line of sight" or "line of vision" refers to a view of a work area by a user. Line of sight may also be referred to as the shortest distance between an eye of a user assuming an ergonomically correct posture and a work area while accounting for any equipment worn by the user intended to re-direct the vision of the user. For example, equipment worn by the user intended to re-direct the vision of the user (e.g., devices described herein) may cause the line of sight to have a longer distance than a direct line between the eye of the user and the work area by virtue of the vision of the user being directed through the equipment, for example, cantilevered imaging modalities.

As used herein, "imaging extension" refers to a forward extending portion of the present devices that supports and positions an imaging modality at a selected distance in front, or forward, of the head (including parts thereof) of a user of the devices.

As used herein, "imaging modality" refers to a camera such as an HD-capable camera or other device capable of capturing images (including videos and/or other representations or depictions, including 3D images) of a work area.

As used herein, "system" refers to an optical device of the present disclosure optionally in addition to hardware, software, firmware, and/or other components (e.g., a camera) in optical, data, and/or auditory communication with the optical device.

As used herein "cantilevered" refers to physical positioning of an imaging modality in a manner that provides or enhances the ability of a user of the device to assume a proper ergonomic posture. In general, "cantilevered" refers to positioning the imaging modality extended in front, or forward, of the head (including parts thereof, such as the eyes, forehead, or face) of the user. A cantilevered imaging modality (e.g., camera), for example, is positioned, and may optionally adjust, on a horizontal plane extending forward from the user so that optimal ergonomic positioning and optimal viewing of the work area may occur.

As used herein, "divergent view" refers to the difference in the direction of the gaze or view of the user versus the line of sight for the imaging modality or optics (including electronic and non-electronic vision embodiments described herein). A divergent view encompasses the idea of permitting the user to assume a comfortable forward-looking gaze or view (i.e., horizontal optical path), while being able to view a work area positioned outside of this forward view or horizontal optical path, such as below the horizontal optical path. As such, in a divergent view, the view direction of the user is different than the view positioning of the imaging modality or optics such that they are divergent from a specific area rather than convergent on a specific area.

As used herein, "add-on device" or "add-on optical device" refers to a specific optical path re-directing device that is provided as an attachment to a conventional optical loupe.

As used herein, "optical path" refers to a straight path through which an image is transmitted, e.g., to a user.

As used herein, "optical communication" refers to communication of an image along an optical path, or between two or more different optical paths. Optical communication of an image (e.g., a work area) can be through lenses, mirrors, prisms, or transmitted through electronic means such as a digital camera, electronic data transmission (including wired or wireless communication), and display of the image. For example, optical communication may refer to two optical paths that intersect (e.g., a work area optical path and a horizontal optical path), or transmitting an image from one optical path (e.g., a work area optical path) to a display or second optical path (e.g., horizontal optical path), or other communication of an image.

As used herein "magnify," "magnifies," "magnification," and "magnifying" refers to enlarging an image, e.g., versus naked eyesight.

As used herein, "viewing portion" refers to a portion of an optical device viewed or viewable by a user when wearing the optical device, such as a lens, mirror, screen, display, or other portion or area of, or defined by, the device. Generally, such a viewing portion is viewable when the user is looking directly ahead, e.g., via a horizontal optical path.

As used herein, "horizontal optical path" refers to the optical path from an eye of a user looking straight out in an "eyes-centered" orientation, for example, as depicted in aspect 20 of FIG. 1.

As used herein, "work area optical path" refers to an optical path with a "work area" being one end-point of the optical path. According to the present disclosure, the work area optical path is generally in optical communication with a horizontal optical path, display, or viewing portion.

As used herein, "eyes-centered" refers a median or natural meridian and longitude orientation of the pupil of an eye of a user. Often, an "eyes centered" position is understood herein to be opposed to an eye position where the user is looking down, up, or to a side direction. A "centered viewing portion" or "centered display" refers to a viewing portion or display that is viewable by a user via a horizontal optical path or when the viewer assumes an eyes-centered orientation. Displays and viewing portions contemplated in systems and devices herein are generally centered displays or centered viewing portions.

As used herein, "user wearable" refers to a device to be worn by a user. Most typically, user wearable refers to a device or system to be worn, at least in part, on the head of a subject.

The present disclosure provides devices that permit the user to assume an ergonomically correct, upright posture while not compromising visual acuity or magnification. When donning optical loupes there is a tendency to bend at the neck, back, and/or shoulders to move closer to the work area. Also often, assuming such a contorted posture is dictated by the focal length of the chosen magnifying mechanism. The user must bend and move within the focal length of the chosen loupe, e.g., typically 15-18 inches. Bending at the pelvis, neck, or with pelvis and neck causes excessive strain on the human body, particularly the back, neck, and shoulders. When conducting repetitive movements or movements that require moving a person's head up and down or simply maintaining head weight in a static position while bent at the neck and/or pelvis such as those required in common dental and surgical procedures, these strains are magnified over time.

According to the present disclosure, in the case of a dental procedure traditional seating arrangements can be maintained for both the patient and the subject while permitting the user to sit in a neutral position with a straight back and neck, thus reducing fatigue and strain. The optical devices described herein not only permit, but often require, the user to sit properly upright in order to maintain the proper optical pathway to the work area. In certain embodiments, the angulation of vision redirection is adjustable such that the posture of the user may vary from an upright or reclined position to a bent-forward position or the device may be placed at other locations on the head or body of the user. For example, if a horizontal line of sight is maintained, the optical device focuses the vision of the user at an optimal angle and focal length toward the work area. Bending down at the neck or back by the user would frequently inhibit this optimal angle and consequent view of the work area.

Though medical procedures are described or contemplated herein such as general and specific in-office or operating room surgical procedures and dental procedures that benefit from a magnified view of a work area, a variety of additional usages for the technologies described herein are contemplated. For example, the jewelry trade, geology, gemology, watchmaking, laboratory technicians, photography, collectors, printing, dentistry, surgery, biology, chemistry, education, meteoritics, electronics, manufacturing, fabrication, tattooing, ophthalmology, dermatology, reading, writing, law enforcement or military, home images or videography, and/or professional videography, among other usage areas. The electronic vision modalities described herein, for example, have significant utility in the media and entertainment arenas.

In one example, readers and users of mobile devices often have to bend their heads downward to view the page or screen. Often, such people desire to or must wear reading glasses to do so. This may be particularly true for mobile device users as mobile devices continue to have increasingly higher resolutions, permitting increasing amounts of information on a small screen. The present devices permit such people to view papers, books, devices or other things without having to assume an ergonomically awkward position by bending downward at all. For example, according to the present devices and methods, a user can relax in an airplane seat with their head comfortably resting against the headrest, looking forward, having a book comfortably lying in their lap, and having their arms comfortably resting at their side, while having full view of the book on their lap. In addition, mobile device users can, for example, watch a show or movie, or read on their mobile device while sitting anywhere in this comfortable manner. Including magnification levels appropriate for corrective vision, reading or viewing high-definition mobile device screens is contemplated. In certain embodiments, the magnification of the devices is linked to the screen resolution of the mobile device to provide optimal magnification to comfortably view items displayed on the mobile device screen.

The present devices also ease eye strain. Prior devices require the user to move their eyes to face downward (e.g., declination of the eye or declination angle) to view through a downward angled loupe. In contrast, the present devices permit the user to assume a comfortable eye position, looking forward (e.g., horizontally forward) rather than downward while being able to clearly view a work area positioned below the eye level of the user.

FIG. 1 depicts a person (24) in a seated position looking horizontally forward (20) with a straight neck, shoulders, and back. Angle (22) defines a desired angulation of the optical path (21) to permit the person (24) to see object (23) without having to bend at the neck, shoulders, or back while continuing to look forward.

The devices of the present disclosure includes a light for illuminating a work area. One or more lights may be provided each having variable or different strengths, positions, or angulations. Often, the light emits a light signal in the visible spectrum, though other light sources are contemplated having additional functionality, such as curing resins and composites, activating photosensitive materials present in the work area, or deactivating photosensitive materials present in the work area. As such, a different or an additional light source can be incorporated in the same or different location on the visor portion such as an ultraviolet light, a quartz-halogen light, a laser, a plasma arc curing light, an LED light, or other light known in the art. Regardless of the light source on the device, if the user operates a light source whose emissions may injure the eyes of the user, it is often important to include a shield or smart glass technology that protects the user's eyes from such emissions. A removable or movable shield may be provided on or with the device, or smart glass that provides a blockage or reduction of damaging light from passing through to the user. In embodiments where the display prohibits sight therethrough, the signal passed through to the user from the camera (e.g., 180° or 360° camera) frequently protects the eyes of the user by blocking incoming damaging light and only passing through a filtered and nondamaging signal to the display.

A variety of magnification levels are contemplated for the presently described optical devices. For example, the device often imparts between about 1.0× to about 8.0× magnification. Often the magnification level is 0.5×, 1.0×, 2.0×, 3.0×, 4.0×, 5.0×, 6.0×, 7.0×, 8.0×, 9.0×, or 10.0×. Enhanced magnification levels may often be achieved through, for example, the use of a high-definition (HD) camera and digital zoom technologies to provide magnification well beyond 10.0× magnification, for example, about 20×, 30×, 40×, 50×, 60×, 70×, 80×, 90×, or 100× undeteriorated magnification. Optical zoom technologies are also often employed to provide an undeteriorated image. In certain embodiments, magnification of up to about 150×, 200×, 250×, 300×, 350×, or 400× is provided using an HD camera, optical, and/or digital zoom. Often, the magnification level of an optical device is selected based on the optical loupe for which it is intended to attach to provide the same or greater level of magnification provided by the optical loupe, most often along a longer focal length.

Frequently, assuming a proper ergonomic posture is mandated through the use of optical devices of the present disclosure. In such embodiments, the user achieves an optimal viewing angle of a work area while keeping their head upright and looking forward. Simply looking forward through the optical device provides an angulation of the line of sight of the user around an optic axis downward toward the work area.

For devices described herein, proper angulation of the line of sight is often dictated by the body type of the user, including accounting for arm length, torso length, neck length, head height, etc.; in addition the relative distance of the work area from the head of the user may be evaluated. In general, angulation of the line of sight varies between about 20 degrees to about 90 degrees versus a horizontal line of sight. Often, the angulation is about 60 degrees to about 80 degrees. Also often, the angulation is about 45 degrees to about 70 degrees. The angulation is often about 20, about 25, about 30, about 35, about 40, about 45, about 50, about 55, about 60, about 65, about 70, about 75, about 80, or about 85 degrees versus a horizontal line of sight. As the increments above are listed in 5 degree increments, it is expected that the use of the term "about" refers to an angulation variability that accounts for the specifically listed degree in addition to the range between degree increments.

Adjusting focal lengths versus the focal length of an existing optical loupe is occasionally necessary due to the further distance of the user from the work area when used in an ergonomically correct position. As such, in certain embodiments this lengthened focal length is achieved by way of an additional magnification, for example a lens, which is provided in the optical device. Where an existing focal length is 18 inches, for example, the focal length may be lengthened by, for example, 6-20 inches, or 10-30 inches to provide a focal length of between 24 inches and 48 inches. The focal length often varies between about 18 inches to 60 inches. The focal length may be longer. As such, the focal length will generally increase by a certain determinable factor, which could be about 1.0×, about 1.1×, about 1.2×, about 1.3×, about 1.4×, about 1.5×, about 1.6×, about 1.7×, about 1.8×, about 1.9×, about 2×, about 2.1×, about 2.2×, about 2.3×, about 2.4×, about 2.5×, or longer, versus the existing focal length of the loupe prior to including the optical devices of the present disclosure. As with the angulation discussed above, the use of the term "about" refers to a focal length distance variability that accounts for the specifically listed distance in addition to the range between distance increments.

Focal length is the distance from the eyes to the work area or object. In certain embodiments, a discrepancy of small distances in designed focal length versus how the devices are utilized (i.e., the actual use distance) can cause eye strain to try to focus.

It is frequently preferred to select a focal length to match the activity that is to be undertaken using the devices described herein. As such, related measurements to determine optimal focal length often occur in the environment where the activity is to take place. Such measurements are often taken using known parameters to ensure proper posture of the user relative to the work area.

The devices contemplated herein may have a distance accounting for a depth of field or working range to ensure that multidimensional work areas are in focus across the entire work area. Often, magnification has an effect on the depth of field or working range such that larger magnifications provide for a smaller depth of field or working range.

In the devices discussed herein any of a variety of usability and personalized features may be included. For example, the line of sight angulation is often customizable on the fly or when the device is removed. For example, fine angulation correction or modification is often provided such that when the optical device is used, the line of sight angulation (e.g., downward angulation relative to a horizontal optical path) may be changeable by the user within an often predetermined range, e.g., 0.1-45 degrees or across a 20-90 degree range, or a 35-90 degree range, or a 45-90 degree range, or a 45-100 degree range, or a 50-80 degree range. A variety of mechanisms are used for customization, including ratcheting mechanisms, friction based rotation, flexible fittings, screw fittings, bolts, clamp-fittings, etc. In certain embodiments, a flexible or rigid light pipe is provided. Often, though it is not required in certain embodiments, an easy to use mechanism is provided to permit angulation customization such as a dial, handle, or similar device. Another frequent feature is a light such as an LED to provide an optimal viewing environment. Contemplated lights are often center-mounted or mounted on or near the outside of the frame holding the device. In certain embodiments, light is provided through the same pathway as the optical pathway of the user such that light passes through the optical system of the device.

To achieve the angulation of the line of sight in any of the variety of lens and prism embodiments discussed herein, often an optical prism (see, e.g., FIG. 2, element 72) or other optical element is utilized. In certain embodiments, an object of the prism or optical element is to provide optical axis angulation, and optionally to produce inversion and/or reversion of the work area image. Certain prism or optical element systems, for example, those described in U.S. Pat. Nos. 2,472,600, 4,232,943, 4,902,116, 5,838,504, 6,198,581, 6,366,411, 6,549,337, 7,184,208, 7,212,353, 7,889,429, 8,749,890, or 8,830,588 maybe used or adapted. Other conventional image rectifiers or inversion features or devices are contemplated. In certain embodiments, the device comprises a lens, a mirror, and a second lens and/or prism such as a roof prism that provides image inversion or reversion so that the image viewed through the device is in the same orientation as the user is or desires. As such, in certain embodiments, the line of sight angulation is provided by a mirror. Magnification and image orientation correction if needed are provide by additional lens or lenses. In certain embodiments, multiple lenses providing magnification at the same or different levels are provided in a device. Often, an optical loupe provides a first level of magnification and the add-on optical device provides a second level of magnification or demagnification.

As the ergonomic optical loupes are intended to be worn on the head of a user, small size and/or light weight are important. Plastic optical elements are often preferred to reduce weight, though glass elements may also be used. Overall, optimal visual acuity is maintained through the use of plastic and/or glass optical elements. The device is often adapted to account for any additional weight or leverage caused by the line of sight angulation elements such that it is weighted to sit evenly on the user's head.

Figure 2:
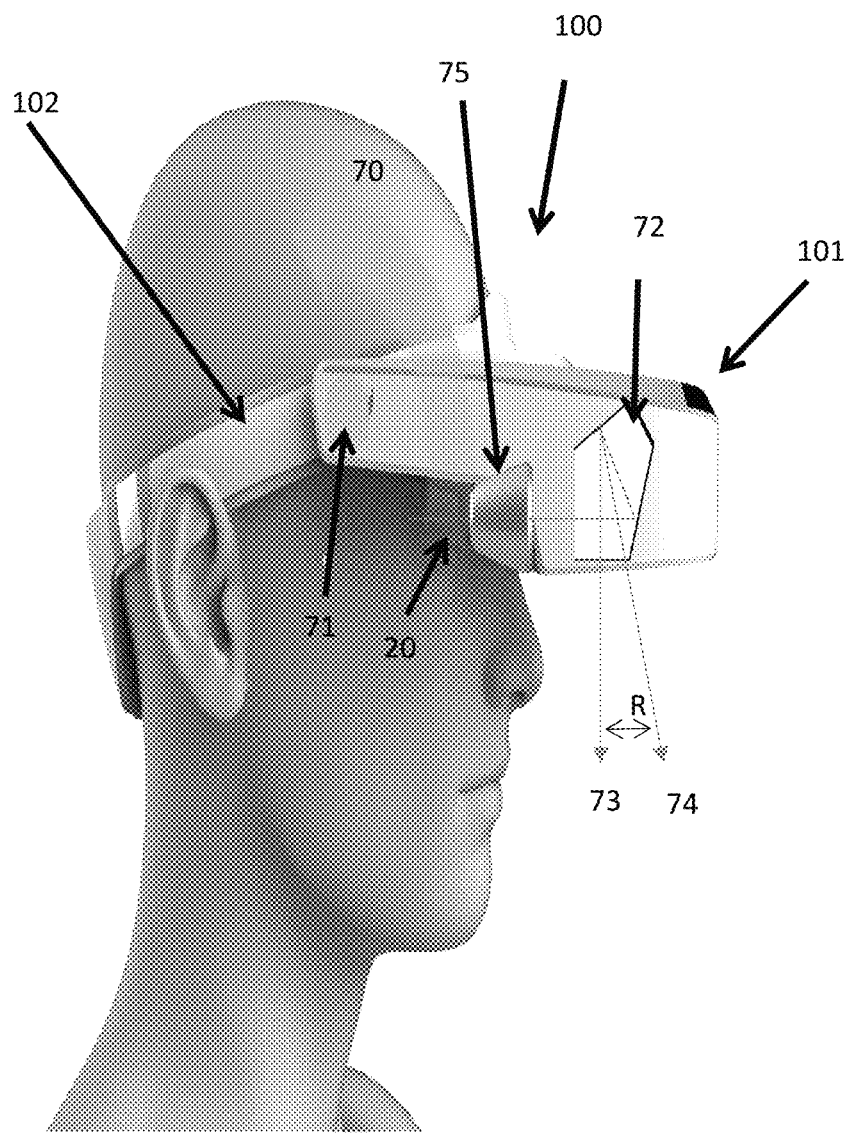
FIG. 2 depicts an exemplary device of the present disclosure containing a prism in operation. As depicted, "represents an option of adjustability in the angle of sight redirection in exemplary embodiments, for example, by tilting the prism.

FIG. 2 depicts an exemplary device of the present disclosure. In this device (100), a visor portion (101) and a headband portion (102) are provided. As depicted, the visor portion (101) is separately movable from the headband portion (102), where it translates from a working position to a retracted position, or vice-versa, along axis (70) about hinge (71). The retracted position may vary provided that the visor (102) is out of the line of sight (20) of the user. Though vertical translation of the visor is depicted, this translation angle may vary. For example, horizontal flip-up translation may be provided using a hinge having horizontal and vertical translation capability on one side of the head band portion (102). Alternatively, the visor portion (101) may translate across the head band portion (102), while translating the head band portion (101) away from the line of sight (20) of the user. Translation may be manual or automated, and a locking mechanism is often provided to hold the visor portion in the working position and/or retracted position, or at a position between a working position and a retracted position. In certain embodiments, the visor portion (101) is attachable/detachable from the headband portion (102) by the user. Though the working position is depicted at a certain location, this location may vary provided that when in the working position the line of sight (20) of the user is redirected through the visor portion. In this exemplary embodiment, a loupe portion (75) provides magnification as described herein, and a prism (72) is provided to redirect the vision of the user to a determined work area. In certain embodiments, mirrors and/or lenses are provided to redirect vision instead of, or in addition to, a prism (72).

Though a prism is depicted in FIG. 2, another optical element such as a pentamirror or another optical element may be utilized as contemplated herein. When the optical element is a prism it is often a pentaprism or another optical prism, which may be comprised of glass, plastic, another optically-clear material, or mixture or combination of materials. Often, an optical element, or materials utilized in the optical element, is utilized that minimizes the weight imparted by the optical element. In certain limited embodiments, the optical element is a concave mirror. It is contemplated that additional lenses, mirrors, and/or filters are utilized in the light path in addition to the optical element or exemplary prism to enhance or preserve visual acuity in the work area. Vision redirecting mechanisms contemplated herein often comprise an optical element.

The vision redirection angulation may be variable along angle "R," between different redirection positions (73, 74). Angle "R" is variable and is represented as a straight line, but "R" refers to the angle created between redirection positions (73, 74). Though redirection in a 90 degree angle (73) and another angle (74) is depicted, the vision redirection may vary over a larger range as discussed herein (e.g., greater than 0 degrees to about 180 degrees) while the user maintains an ergonomic position with eyes facing directly forward from the head of the user (e.g., a horizontal optical path or an eyes-centered position).

Figure 3:
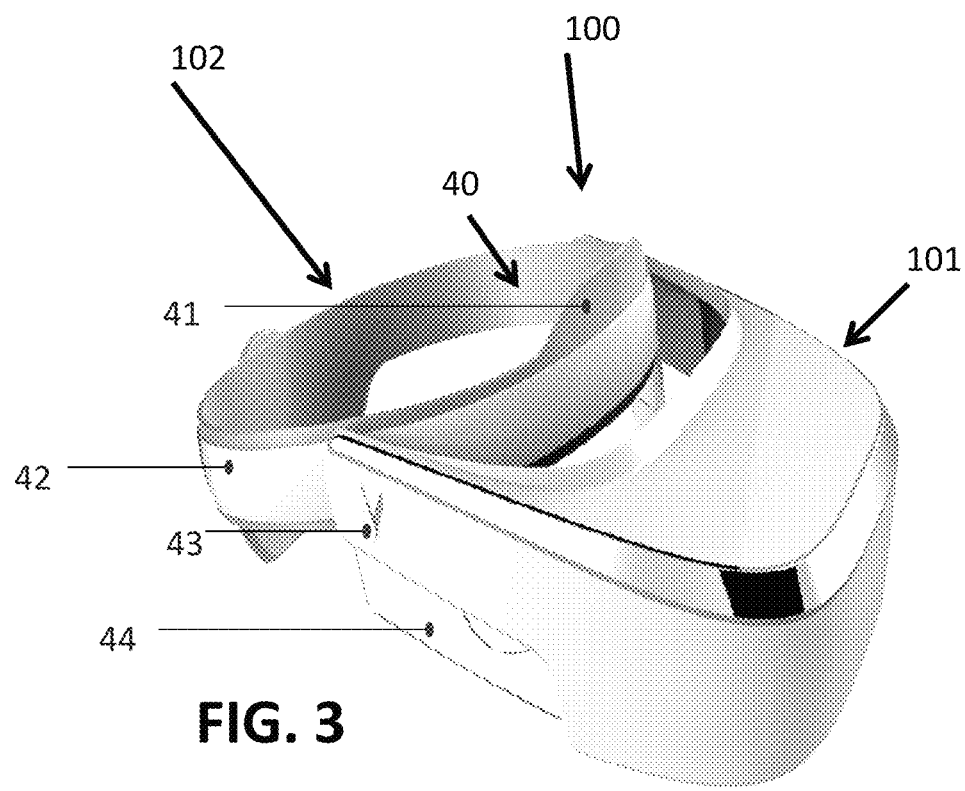
FIG. 3 depicts a view of an exemplary embodiment of a device of the present disclosure.

FIG. 3 depicts another view of an exemplary device (100) having a headband portion (102) and a visor portion (101). The headband portion (101) is provided in this example with certain fitting and wearability features such as a brow pad (41). The brow pad (41) and/or the remainder of the inside (40) of the headband portion may be padded, have a larger profile versus other portions of the headband (102), insulated, actively heated or cooled, and/or provided with moisture absorbing or moisture wicking capability to maintain comfort of the device for the user when used over prolonged periods of time or use in different environments such as hot or cold environments. The brow pad (41) often has an expanded profile, for example, to spread the pressure of the device across a larger area of the head of the user. In this exemplary device, a side shield (44) is provided such that the user can maintain peripheral vision capability while the visor is in the working position. The side shield (44) is often transparent, tinted, mirrored, or provided with smart glass technology to provide both additional side protection and the ability to see through it. A switch (43) for operating another aspect of the device. This switch (43) may be a button, switch, dial, capacitive sensor, touch screen, other mechanical or electronic mechanism, or the like. The switch (43) in one exemplary embodiment, operated to turn on a light such as an LED light to illuminate a work area. Other types of lights may be provided, such as lasers, ultraviolet light, plasma arc curing light, blue light, or other light to provide additional functionality such as for curing resins or conducting specific exams such as, for example, oral cancer exams. Light for exciting a fluorescent dye or marker may also be provided such that the dye or marker may be viewable by the user. Light for activating another photosensitive material such as a photo-cleavable bond may also be provided.

The switch (43) may also (alternatively or in addition) be provided to prompt the visor to translate to or from a retracted position. Voice activation may also, or alternatively, be provided for this and other aspects of the present embodiment. One or more switches (43) for operating another aspect of the device may be positioned on the visor portion (101) or the headband portion (102). The switch (43) may also be provided to adjust the line of sight angulation between different angles, to adjust the level of magnification, adjust the focal length, and/or another adjustment.

Figure 4:
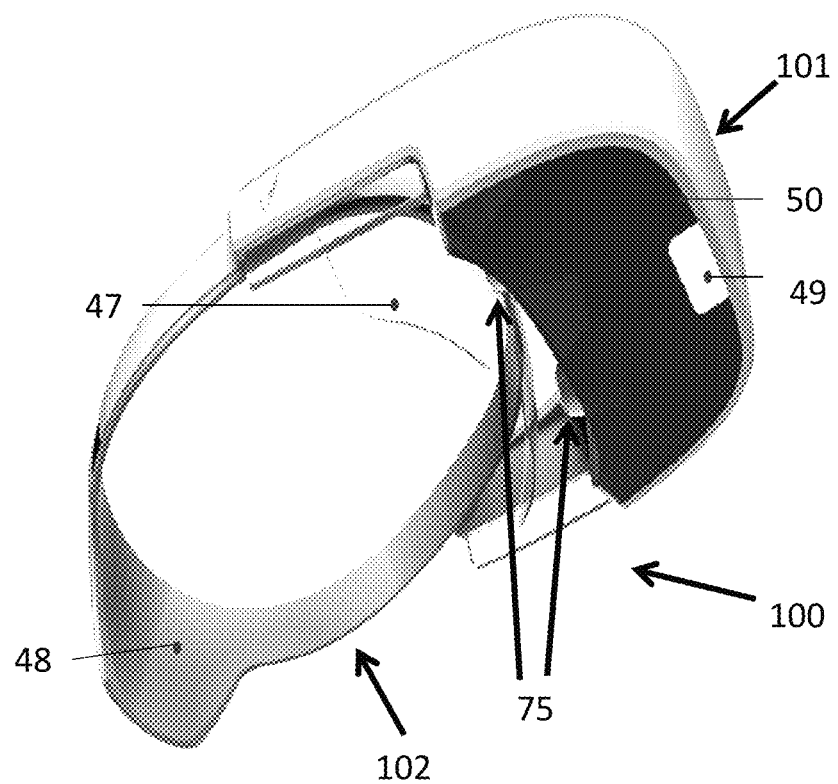
FIG. 4 depicts another view of an exemplary embodiment of a device of the present disclosure.

FIG. 4 depicts an exemplary device (100) having a visor portion (101) and a headband portion (102). A front shield (47) is provided that is transparent, tinted or mirrored. In certain embodiments, the front shield permits the user to view a photoactivated or chemically activated substance such as a chemiluminescent or fluorescent dye. The front shield (47) provides additional protection of the users face and eyes from liquids or debris, and also often provides additional structural rigidity to the device (100). The front shield (47) may be provided such that it does not contact the face of the user (depicted), but may also be provided or oriented such that it rests on the face of the user, for example on the nose of the user similar to a pair of traditional spectacles. As depicted, the front shield (47) is separate from the loupe portion (75), which is positioned in the visor portion (101). However, the loupe portion (75), in certain embodiments, may be attached (movably or fixed) to, or pass through, the front shield (47), or it may be separately positioned attached (including movably attached) to the headband portion (102) or the visor portion (101).

The visor portion (101) includes a light (49) for illuminating a work area. One or more lights maybe provided each having variable or different strengths, positions, or angulations. Often, light (49) emits a light signal in the visible spectrum, though other light sources are contemplated having additional functionality, such as curing resins and composites, activating photosensitive materials present in the work area, or deactivating photosensitive materials present in the work area. As such, a different or an additional light source can be incorporated in the same or different location on the visor portion such as an ultraviolet light, a quartz-halogen light, a laser, a plasma arc curing light, an LED light, or other light known in the art.

The front shield or side shield (i.e., primary shields) may be provided in a manner that provides protection from errant light outside of the visible spectrum that may be harmful to the user. Often, either or both shields are provided with a coating that blocks harmful light signals or radiation signals from reaching the user such as X-Rays, UV light, blue light, laser light, or other high intensity light. Also often, either or both shields are removably attached to the device to permit a shield adapted to block harmful light signals (e.g., a light or radiation protective shield to block, for example, X-Rays, UV light, blue light, laser light, or other high intensity light) to be attached to the device such that the user may utilize the same device and attach either or both shields while wearing the device or by removing the device to replace either or both shields. In certain embodiments, a separate attachment area is provided to insert a light protective shield into the device without removing the primary front or side shield. Often, this light protective shield is placed adjacent to an existing shield. In certain embodiments, the light protective shield is built into the visor portion in a permanent or removable manner, for example at underside (50) (see FIG. 4) of the visor portion. In certain embodiments, a light protective shield is built into the device (e.g., as part of the head band, primary shields, or visor portion) that is actuatable by the user, for example by touching or pressing a button, turning a dial, or the like, on the device. The actuation of the protective shield yields movement of the protective shield into or away from the light path between the user and the work area. Though described in connection with the headband and visor embodiment, the protective shield is often applied in other embodiments described herein.

At least a portion of underside (50) of the visor portion (101) is often provided with a tinted or mirrored finish such that light may pass through to the eye of the user, but prohibit viewing the eye of the user from below of the underside (50). The underside (50) may also comprise a smartglass technology as contemplated herein. In certain embodiments, the underside (50) of the visor is provided with a mechanism to display a message or image viewable from below the underside (50) that may be provided or adjustable by the user, another person, or a computer. The skull base portion (48) of the headband portion (102) is often provided with an expanded profile to spread the contact area of the headband portion (102) over a larger area of the head of the user. Often, the expanded profile is provided since a battery pack or another feature is provided at this location of the headband portion (102). The skull base portion (48) may be padded, insulated, actively heated or cooled, and/or provided with moisture absorbing or moisture wicking capability to maintain comfort of the device for the user when used over prolonged periods of time or use in different environments such as hot or cold environments.

Figure 5A:
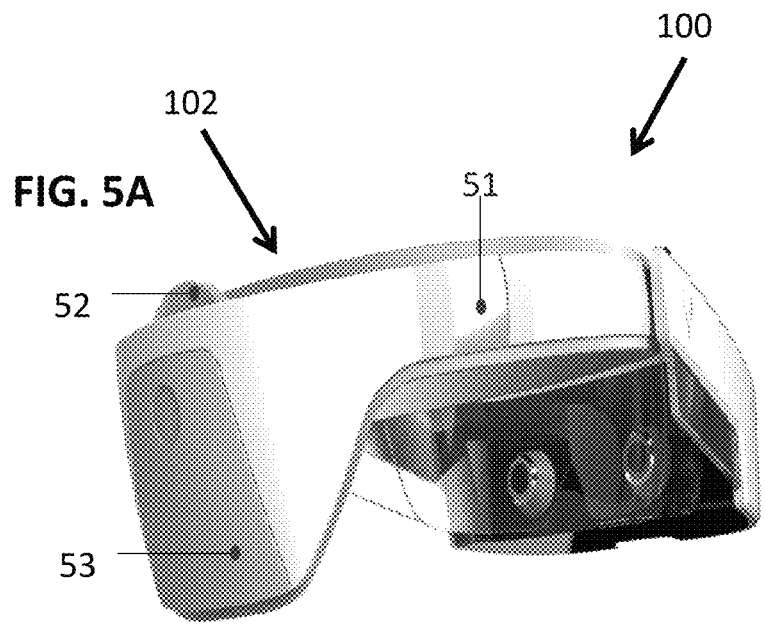
FIG. 5A and FIG. 5B depict other views of an exemplary embodiment of a device of the present disclosure.
Figure 5B:
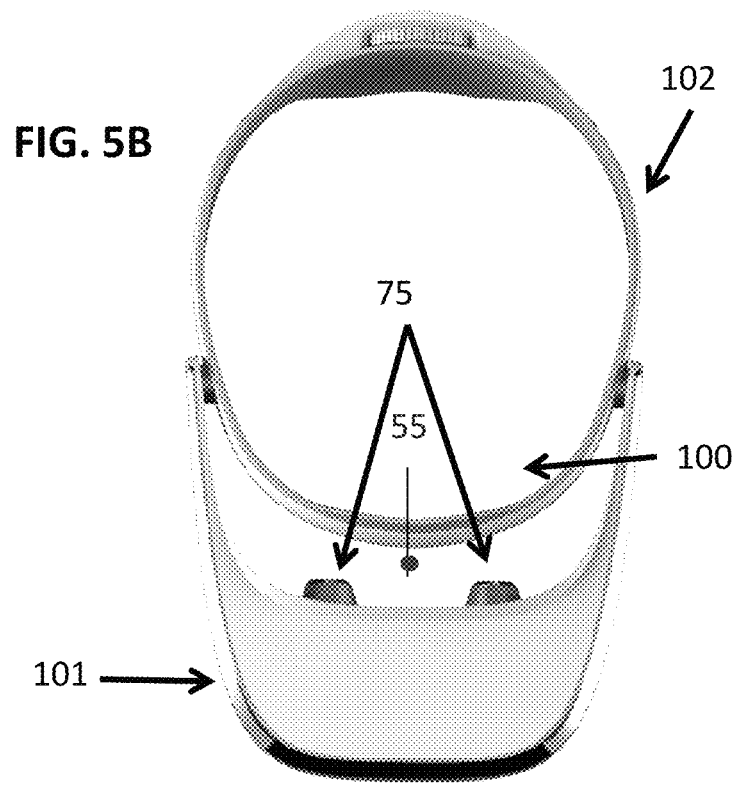

FIGS. 5A and 5B depict additional views of an exemplary device. A battery pack (53) is provided removably attached to the headband portion (102). An exemplary battery in the battery pack (53) is often rechargeable and provided with sufficient power to power a light, and any additional features such as sensors, switches or displays over a prolonged period (e.g., hours, days, or weeks). The battery pack (53) is removable for convenience or to permit a hot-swap of batteries, for example, while a user is wearing the device (100). A battery power meter (not depicted) is also often provided on the battery pack (53) or the device (100) to permit a user or another person to determine the power level of the battery. In certain embodiments, battery power level in the batter pack (53) may be remotely monitored during use or while charging, for example, using BLUETOOTH® technology or the like. As also depicted in FIGS. 5A and 5B, a headband portion (102) fit adjustor (52) is provided to adjust the circumference of the headband portion (102). The fit adjustor (52) is depicted as dial, but other mechanisms are contemplated. The fit adjustor (52) operates in conjunction with an adjustable portion (51) of the headband portion (102), such that operation of the fit adjustor (52) causes the adjustable portion (51) to move such that the circumference of the headband portion (102) increases or decreases. The fit adjustor (52) may be positioned in any suitable location on the headband portion (102). FIG. 5B shows a top view of an exemplary device, where the loupe portion (75) is viewable, in addition to an empty space region (55) between the front shield and the visor portion (101). The size of the empty space region (55) may often vary.

Figure 6A:
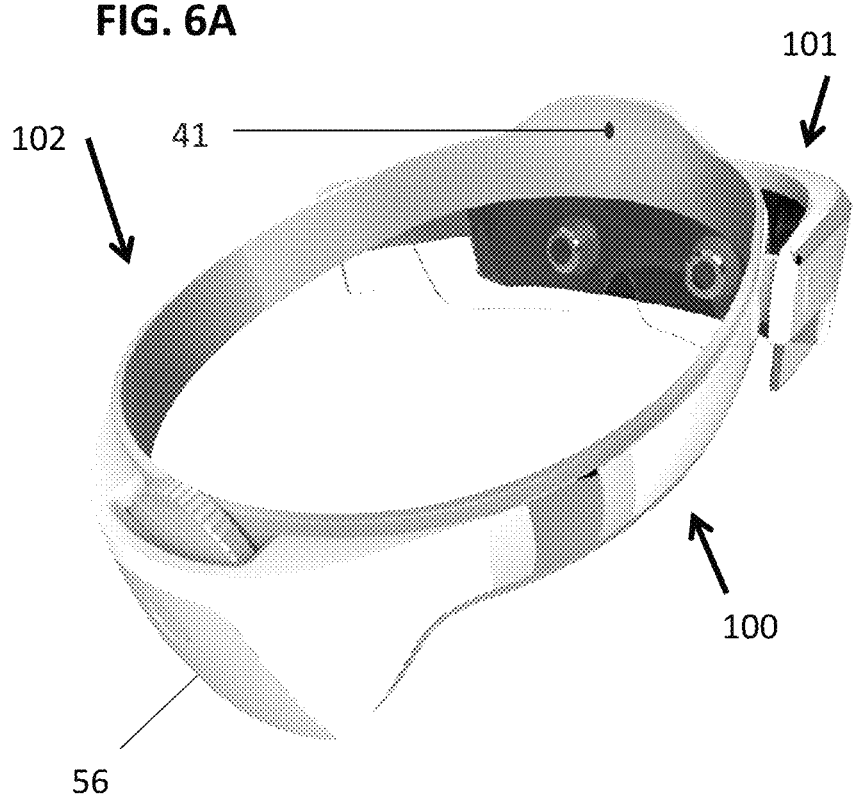
FIG. 6A and FIG. 6B depict other views of an exemplary embodiment of a device of the present disclosure alone (FIG. 6A) and from the back worn by a user (FIG. 6B).
Figure 6B:
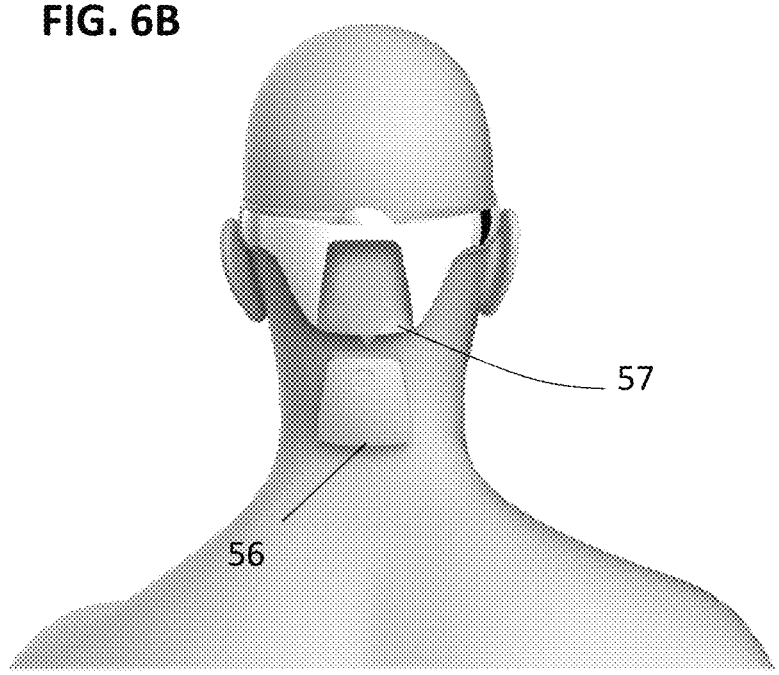

FIG. 6A depicts a slightly different view of an exemplary device versus FIG. 4A, where the brow pad portion (41) is visible. FIG. 6B depicts the detachable functionality of an exemplary battery pack (56) as it is detached from its bay (57) positioned in the headband portion (102) of the device (100).

Figure 7:
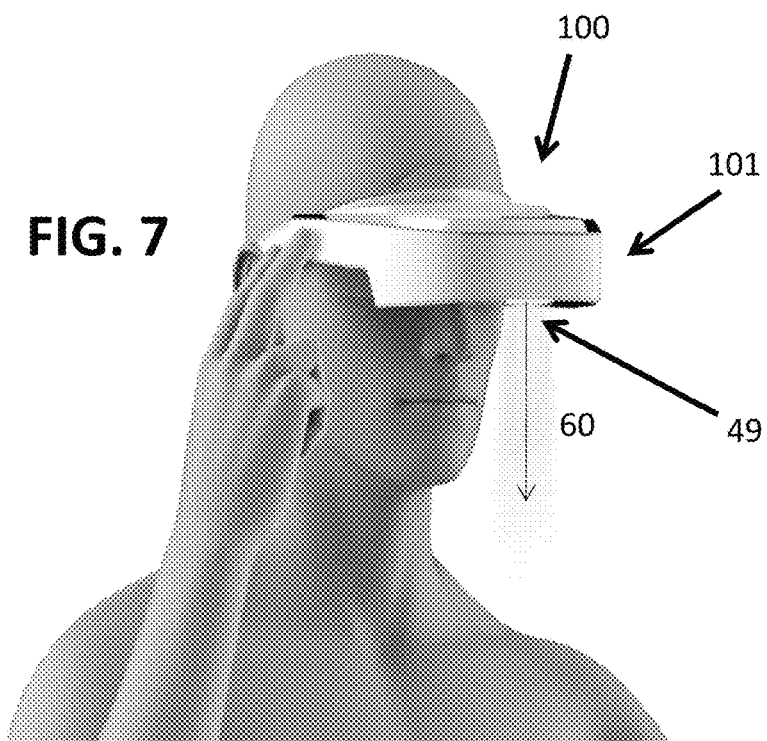
FIG. 7 depicts another view of an exemplary embodiment of a device of the present disclosure worn by a user.

FIG. 7 depicts the functioning of the light (49), as the user touches switch (43) (covered by the hand of the user) on the visor portion (101) to operate the light to direct a beam of light (arrow 60) downward to a work area, following the redirected vision of the user. Arrow (60) in this Figure also depicts approximately the angle of the line of sight redirection provided by the device (100).

Figure 8A:
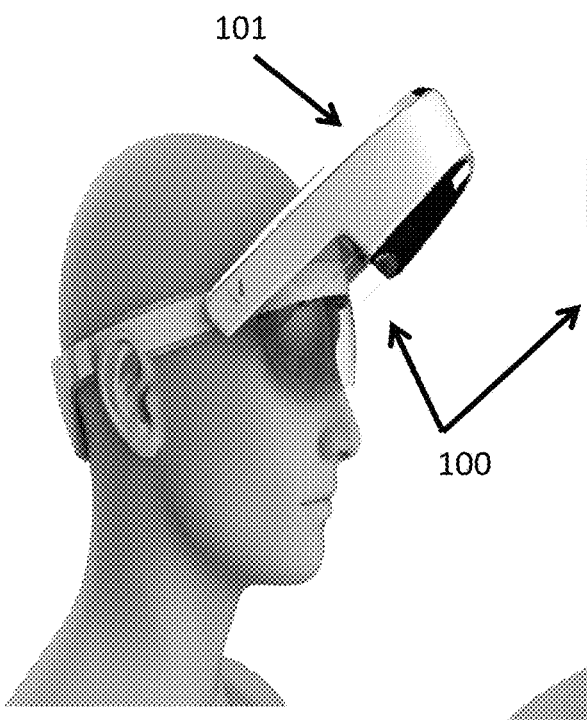
FIG. 8A and FIG. 8B depict another view of an exemplary embodiment of a device of the present disclosure worn by a user. A side view (FIG. 8A) and a profile view (FIG. 8B) are provided.
Figure 8B:
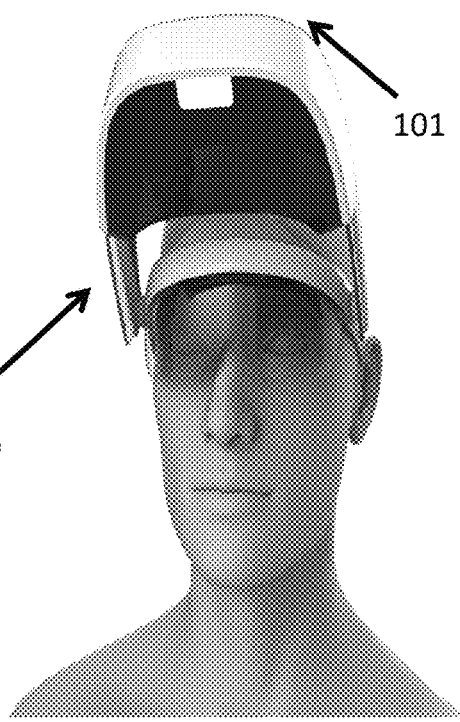

FIGS. 8A and 8B depict different views of an exemplary device (100) with the visor portion (101) positioned in a retracted position.

In one embodiment, an add-on optical device is provided that is adapted to fit on an existing optical loupe. Often, the lens cover of the loupe is removed and replaced with the add-on optical device. The add-on optical device can be mounted through any known means, such as friction fit, screw fitting, snap-fitting, closures, latches, adhesive, ribs, click-fittings, etc. When the device is an add-on optical device, it is often adapted or adaptable to fit a variety of commercially available or custom loupes, generally accounting for the outer diameter or size dimensions of the front of the loupe. In certain devices the add-on optical device can be provide in multiple different levels of magnification such that the same optical loupe can be user, with the add-on optical device providing varied levels of magnification.

A variety of magnification levels are contemplated for add-on optical devices described herein. For example, an add-on optical device often imparts between about 1.0× to about 8.0× magnification. Often the magnification level is 0.5×, 1.0×, 2.0×, 3.0×, 4.0×, 5.0×, 6.0×, 7.0×, 8.0×, 9.0×, or 10.0×. Often the magnification level of an optical device is selected based on the optical loupe for which it is intended to attach (if it is an add-on device) to provide the same or greater level of magnification provided by the optical loupe, most often along a longer focal length. In certain embodiments, the optical device is selected to impart a lower level of magnification than imparted by the optical loupe to which the add-on device is attached. Such embodiments are often desired if the optical loupe provides a larger level of magnification than is desired for a specific application, activity, or procedure. Often the longer focal length imparted by the optical devices described herein result in an inherent increase in magnification, which can be adapted to be decreased and/or focused by the lens choice in the optical device. As contemplated herein, optical devices may also incorporate a detachable or selectable line of sight angulation component that provides the variations of magnification described herein.

FIG. 9A provides a basic diagrammatic representation of an exemplary optical device (200) of the present disclosure. Such a device has a frame (240) for supporting the various features of the device. While the frame may be arranged similar to a pair of spectacles, it may be provided in a variety of formats such as a spectacle frame, visor, helmet, hat, goggles, or other format. Attached to the frame (240) is the imaging extension (230). The imaging extension (230) extends forward of the frame in a position that provides an enhanced viewing angle of the work area. As part of the imaging extension (230) a connection (204) and a support (203) are provided to attach the imaging modality (205) to the frame (240). The imaging modality (205) is cantilevered from the device. The imaging modality (205) is most frequently, therefore, referred to herein as a cantilevered imaging modality or cantilevered camera. The connection (204) may be rigid or manipulatable, referring to whether it provides the capability to move or adjust the support (203) and/or imaging modality (205) in one or more directions. If the connection (204) is of the manipulatable variety, it is often provided such that the support (204) can be adjusted vertically and/or horizontally. The support (204) can also be provided in rigid or extendable forms. In an extendable form, the support (204) can be adjusted to be shorter or longer to bring the imaging modality (205) closer to the frame (240) or user or to extend the imaging modality (205) further from the frame (240) or user, e.g., along reference "T" in FIGS. 10A, 10C, and 11C. The imaging modality (205) is optionally movable along support (203) along reference "T." In certain embodiments, there is no obvious or mechanical distinction between the connection (204) and the support (203) such that the support (203) is extendable or rigid, and/or is rigid or adjustable in the vertical and/or horizontal planes without a separate connection (204). Support (203) can be extendable through any variety of adaptations, alternatively, imaging modality (205) may be movably mounted on support to slide or move between, or attach at, different positions of support (203). The imaging modality (205) in the present embodiment includes an imaging surface (201) and a light source surface (202) including a light source (207, FIG. 10A) such as an LED.

As depicted in FIG. 9A, the imaging modality (205) is a downward facing, or work area facing, imaging modality (205). A prism, for example, is not utilized to re-orient a horizontal-facing camera in the most frequent embodiments. Rather, the lens of an imaging modality is most frequently physically-oriented in a downward manner. Moreover, the imaging modality (205) is extended or cantilevered in front of the user to aid in providing an optimal view of the work area while the user is able to assume an ergonomically-correct posture. In the most frequent embodiments, the camera is the imaging modality (205) and it is oriented such that it faces downward from a horizontal plane, in a different direction than the direction of the user's sight direction. Stated differently, most frequently, the camera is oriented such that it faces a different direction than the view directly from the eyes of the user. For example, where the user is looking horizontal, the camera is facing downward toward a work area such as the mouth of a patient, or a surgical area.

The imaging surface (201) and/or light source surface (202) can be oriented facing downward, angled, or horizontal, for example as depicted in FIGS. 9A, 9B, 10B, and 10C. In general, the path of light emitted from the light source (207) is parallel or coaxial with the imaging path such that light from the light source strikes and illuminates the imaged work area. The imaging modality (205) may also be mounted on the support in a fixed or adjustable manner, for example, to adjust imaging toward or on a work area.

As also depicted in FIG. 9A, the frame (240) includes lenses having outer (210) and inner (220) surfaces. The display (dotted lines in item 210) is embedded within the lens, attached to the lens, or suspended near the inner (220) surface of the lens. In certain embodiments the display is inner (220) surface of the lens. As is depicted, inner surface (220) of the lens is a centered display; this display is viewable by the user when wearing the device via a horizontal optical path. The outer (210) surface of the lens often comprises a smart glass technology, as further described herein, to provide manipulatable clear viewing or light entry or opacity, shading, or light blockage to the eyes of the user. In certain embodiments, a shade may be attached over the outer (210) surface of the lens to limit light entry to the eyes of the user. When smart glass technology is utilized, it is often provided in laminate form or the smart glass forms at least a portion of the lens material.

FIG. 9B provides another depiction of an exemplary optical device. In this device, the imaging modality (205) has an imaging surface (201) that is angled forward to provide a more forward angle for imaging a work area. Though it is not specifically depicted in this view, such an embodiment generally includes a light source as well.

As depicted in FIGS. 9A and 9B, the optical path redirection can be varied, for example along angle "R," between different redirection positions (73, 74). An exemplary horizontal optical path (dotted line 20) is provided in FIGS. 9A and 9B for reference purposes. The embodiments represented by FIGS. 9-11 are represented as a pair of spectacles for exemplary purposes only. Such embodiments can be provided in different user-wearable formats and orientations, and may also be provided with any of the variety of optical device features contemplated herein, e.g., the embodiment represented in FIG. 2.

FIG. 10A depicts the underside of the imaging extension (230) of FIG. 9A. A camera (208), such as an HD camera or other cameras described herein, is provided within the imaging surface (201). The camera is provided in data communication with an imaging system also contemplated herein, often via wireless data connection (e.g., WPAN/Bluetooth, Coexistence, High Rate WPAN, Low Rate WPAN, mesh Networking, Body Area Networks, WiFi, WiMax, other wireless networks, Visible Light Communication, etc.), though corded connection is also contemplated. The imaging modality (205) also includes a light source surface (202) containing a light source (207) such as an LED. The light source (207) illuminates at least a portion of the work area. Though a single light source (207) is depicted, multiple light sources may be provided. Multiple light sources may be the same type of light source or different types of light sources to provide added functionality such as imaging dyes or markers, curing resins, viewing types of dental or oral features or defects, among other functions. The light source (207) most frequently is powered by a dedicated power source such as a battery and is wireless. In other embodiments, the light source (207) and the imaging modality (205) are powered by the same power source. In either implementation, the power source is generally on-board the device and not provided in a corded manner such that the cord is visible, appended to a belt-secured battery, or separate from the device.

FIGS. 10B and 10C provide additional views of alternative imaging extensions (230). Though they are not specifically depicted in these views, such embodiments generally include light sources as well.

Figure 11A:
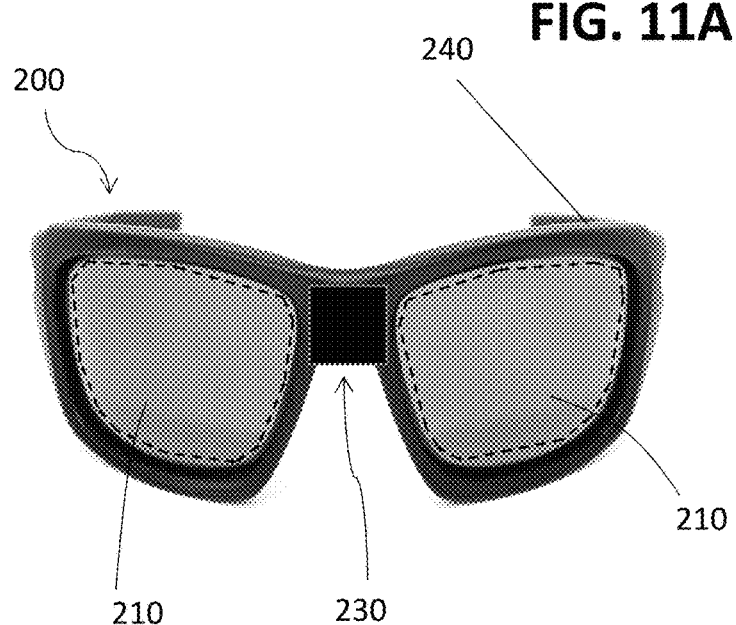
FIG. 11A depicts a front view of another vision re-directing device embodiment.
Figure 11B:
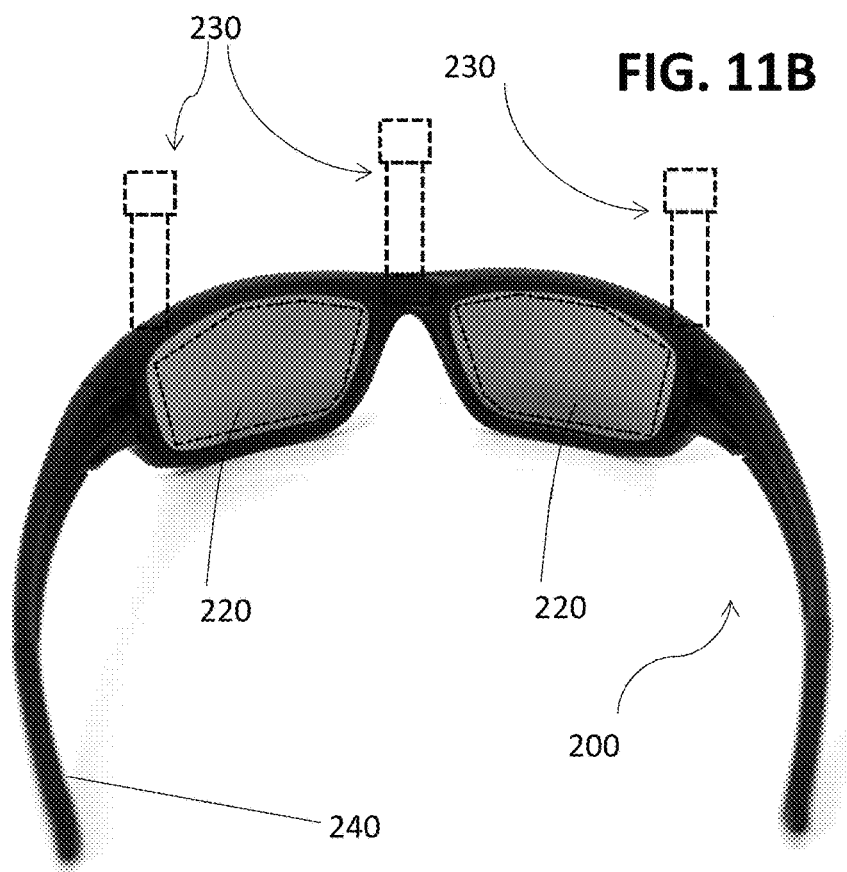
FIG. 11B depicts a rear view of an exemplary vision re-directing device embodiment.
Figure 11C:
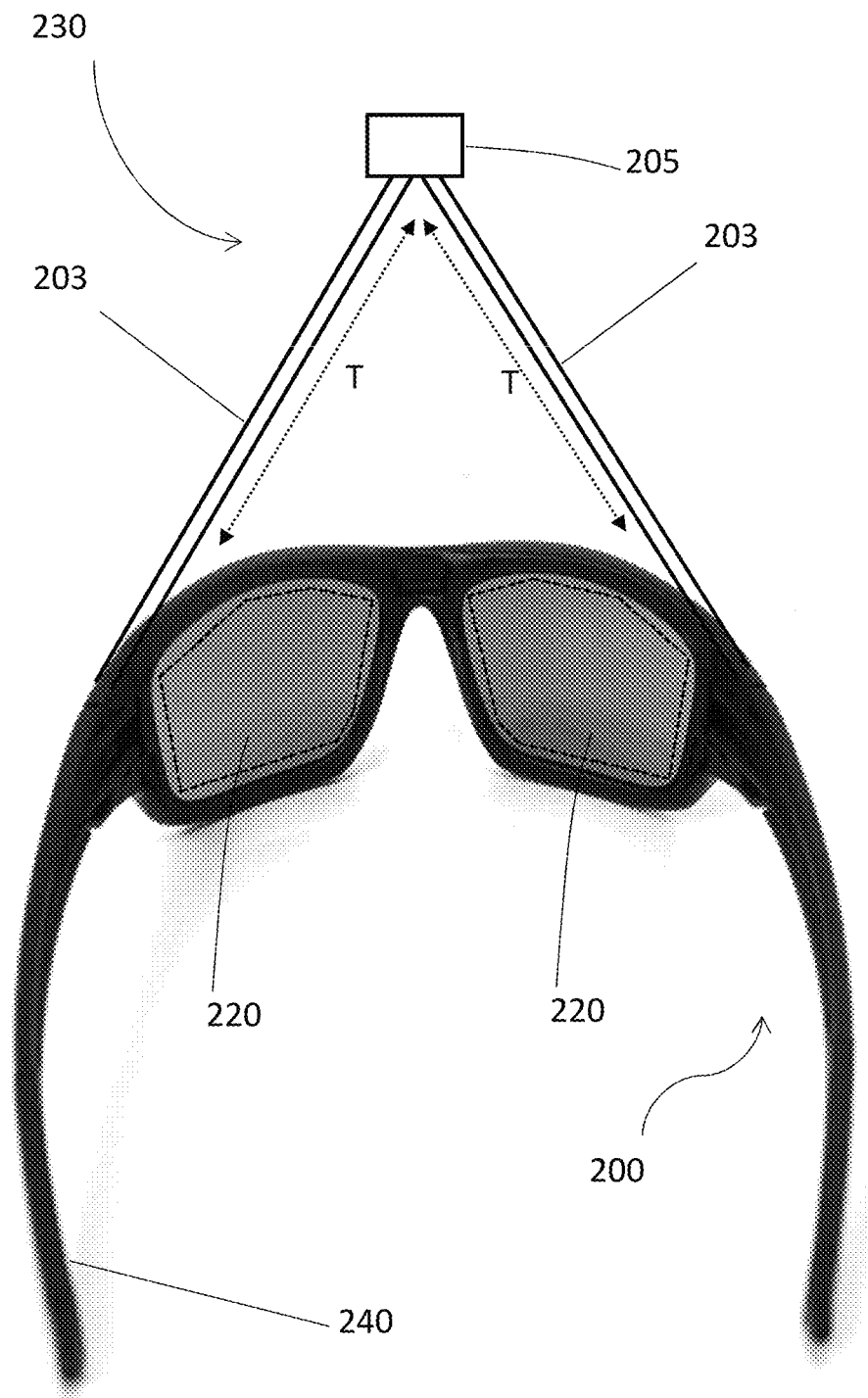
FIG. 11C depicts a rear view of another exemplary vision re-directing device embodiment.

FIGS. 11A, 11B, and 11C depict front and rear views of an exemplary optical device (200), including the features described herein. FIG. 11B depicts optional exemplary placement locations of an optical extension (230) on the device. An optical extension (230) may be placed at any one or more of the depicted locations, or other locations, on the optical device (200) with the provision that it extends forward of the device to provide for the ergonomic benefits of the device (200) as described herein. Multiple optical extensions may be included on an exemplary device (200). Often, when multiple optical extensions are provided, the imaging modalities (e.g., cameras) that are utilized are directed in different, but often overlapping directions. In such embodiments, the imaging hardware, firmware, or software blends the images of the multiple imaging modalities such that the user views a single blended image obtained from multiple imaging modalities. Also, in certain embodiments, each of the multiple imaging modalities provides a different image (e.g., different directions or magnifications) that can be toggled through by the user.

FIG. 11C depicts an alternative cantilevered arrangement of the imaging modality (205). In this embodiment, two supports (203) are provided to position the imaging modality (205). The supports in this embodiment may be independently extendable along axis "T," or the imaging modality (205) may be positioned along the length of either or both supports (203).

Figure 12:
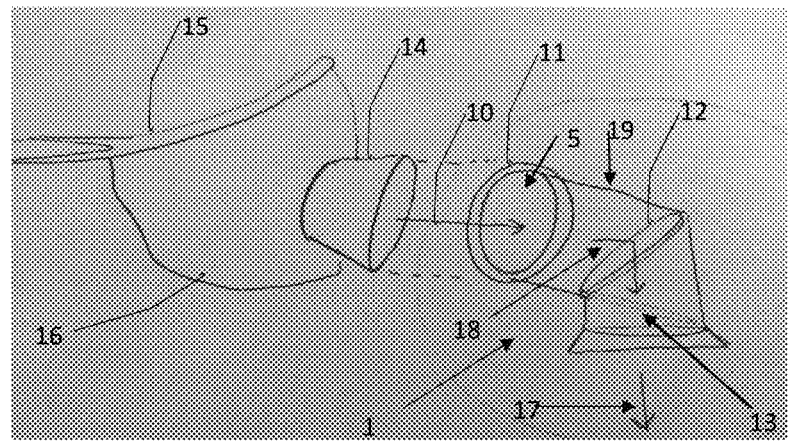
FIG. 12 depicts a profile of an exemplary add-on device.

FIG. 12 depicts an exemplary non-electronic add-on device (1) detached from an optical loupe (14) held in spectacles. Frame (15) supports the lens (16) of the spectacles. Housing (19) holds the optical elements (5, 13) can be one or more lens, and optical element (12) can be a mirror, diagonal or prism. In certain limited embodiments, the optical element is a concave mirror. When the optical element is a prism it is often a pentaprism or another optical prism, which may be comprised of glass, plastic, another optically-clear material, or mixture or combination of materials. Often, an optical element, or materials utilized in the optical element, is utilized that minimizes the weight imparted by the optical element. Vision redirecting mechanisms contemplated herein often comprise an optical element. The optical path is defined by arrows (10, 17, 18). Optical path 10 is not a "horizontal optical path" as that term is used herein. Optical path 10 and optical path 20 (e.g., FIGS. 2, 9, 13, 14) are not the same optical path. Rather, optical path 10 refers to an optical path passing through a "conventional" Through-The-Lens or Flip-Up loupe/telescope (e.g., available from Orascoptic, Designs for Vision, Inc., SheerVision, Inc., Perioptix Inc., SurgiTel, among others). In operation, conventional Through-The-Lens or Flip-Up loupes/telescopes do not permit a user to assume an eyes-centered position. Optical path 10, therefore, only refers to add-on optical device embodiments described herein. The angulation depicted in arrow (18) depicts an exemplary change in optical path from one angle to another angle relative to horizontal. Outer portion of the housing (11) is provided to attach to the loupe (14), fitting around the outside of the housing of the loupe (14). Though a light source is not depicted, it is typically included and can be mounted, for example, in the spectacle frame (15), on the lens (16), on the loupe (14), or on the add-on device (19).

Figure 13:
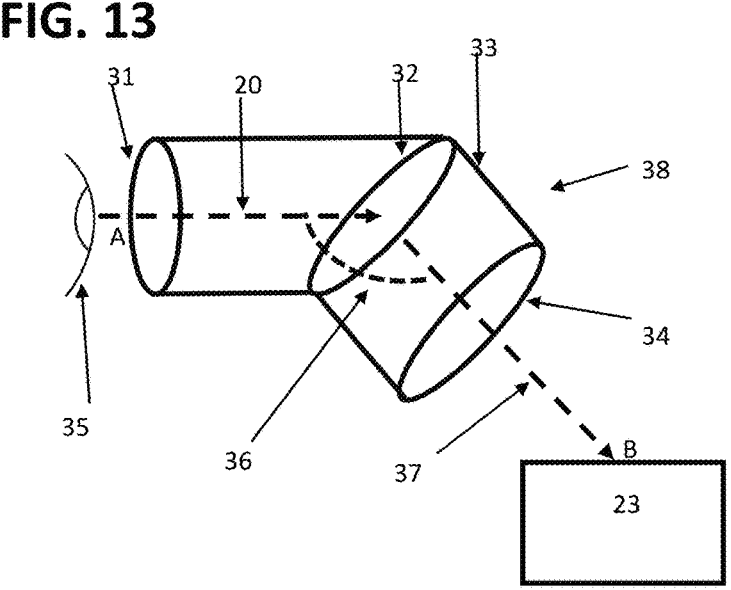
FIG. 13 depicts a operable diagrammatic view of another embodiment of a device of the present disclosure.

FIG. 13 depicts a basic operative view of an exemplary non-electronic optical device (38). Optical path is depicted by first and second paths (20, 37) having a focal length extending between an eye (35) to an object (23). This optical path is defined by the span between (A) and (B) and defined by a first path (20) and a second path (37). It is understood that a focal length may also be understood to extend from a point internal to an eye or its nerves rather than the outermost portion of the eye, which is contemplated herein, as such, the focal length (A to B) is provided for ease of reference. Angle (36) defines an angulation of the optical path from horizontal as defined by first path (20) to downwardly angled defined by second path (37). The depicted optical device (38) contains optical elements (31, 32, and 34) as described herein within its housing (33).

Figure 14:
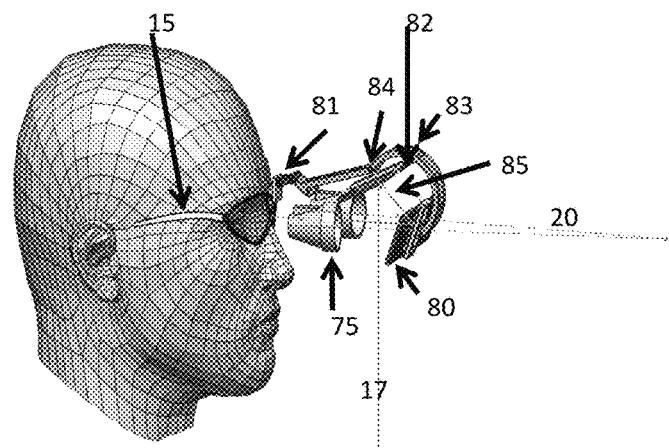
FIG. 14 depicts a operable diagrammatic view of another embodiment of a device of the present disclosure.

FIG. 14 depicts another device embodiment. As depicted, a support (83) is attached to an eyeglass frame (15) through a linkage (81). Support (83) includes mirrors (80, 82) for redirection the vision of the user after passage through loupes (75), from a first optical path (10) to an adjusted optical path (17). Transitional optical path (85) defines the optical path between the first and second mirrors (80, 82), which is most frequently maintained as a constant despite any adjustments to linkage (81) or junction (84). Often, when mirrors are provided, they are provided in an orientation that replicates the orientation of internal reflecting surfaces of an optical prism described herein such as a pentaprism. The first mirror (80) and the second mirror (82) are often attached to support in an adjustable manner to provide for fine-tune corrections or adjustments to maintain the integrity of the adjusted optical path (17). Though only two mirrors are depicted, frequently 4 mirrors are provided in two pairs, each pair defining an individual optical path, one corresponding to each eye of the user. The specific number of mirrors utilized is less important than visual acuity and image orientation, therefore each of the individual optical paths generally converge at the work area focal length so that only a single image is seen by the user while using the device. Linkage (81) may be provided in an adjustable manner such that support (83) can be moved out of the line of vision of the user. Often, junction (84) is provided that permits adjustable vertical orientation of the mirrors (80, 82), while the first optical path (20) remains the same. Often, when the orientation of the mirrors (80, 82) is adjusted, the first optical path (20) continues to intersect with the first mirror (80). In this manner, the angulation (see, e.g., FIG. 2, element "R") of the adjusted optical path (17) be varied while maintaining the horizontal (or ergonomic) integrity of the first optical path (20). Junction (84) is often a hinge, though other movable or adjustable means are contemplated. The adjustment of junction (84) may be manual or automated.

In general, devices of the present disclosure are provided or implemented in a manner that is compliant with all Federal Regulatory laws and rules as medical devices (e.g., HIPPA compliant, FDA compliant, Health Ministry compliant, etc.). For example, the present devices are implemented to ensure safe use for the user and patient or subject, including protection of the health (e.g., eyes, skin, mucosa, etc.) of the patient.

In certain frequent embodiments, a device described herein includes one or more of a variety of electronic vision options. In certain embodiments, a camera (often an HD camera, camera capable of capturing digital images, or other imaging device—together referred to herein as a "camera") is the electronic vision option and is focused through the line of sight. This camera, for example, is capable of taking still images or video capture. Generally, cameras contemplated herein provide for electronic image capture and are often operably linked with firmware and/or software with an application that permits electronic magnification of captured images. Such cameras are also often operably linked with a database or storage medium that permits storage of selected images, series of images and/or videos captured with the camera. The term "image" or "images" as it refers to information captured by cameras described and contemplated herein is, unless specifically indicated otherwise, intended to include still-capture and video-capture.

Cameras contemplated for use in the devices described herein are compact or miniature, such as the size of an HD camera resident on a mobile device such as a smart phone, tablet, or laptop. Often, the camera is capable of capturing 8 MP, 12 MP, 16 MP, 16.3 MP, or more detailed pictures. Also often, the camera is capable of capturing 720i, 720p, 1080i, 1080p, or 4K video captures. In certain embodiments, the camera is capable of capturing up to about 20 MP, 30 MP, 40 MP, or 50 MP images.

In certain frequent embodiments, the camera is a 180° camera, capable of viewing up to 180° and zooming in within discreet areas of the viewing area. In certain other embodiments, the camera is a 360° camera, capable of viewing up to 360° and zooming in within discreet areas of the viewing area. Often, in such embodiments, the user can select a portion or region of the 90°-180°, or 180°-360°, view to focus on or to magnify, often via digital magnification. Occasionally, in such embodiments the display may be provided in a manner that does not permit the user to view through the display, though see through displays may be frequently employed.

The operation of the camera in such embodiments often involves line of sight angulation and magnification as described herein. Alternatively, the camera can be provided in an angle that does not require line of sight angulation, but permits the user to assume an ergonomically correct or appropriate posture when viewing a work area. According to the present disclosure, the camera is often adapted to have a pre-determined or adjustable focal length. Also, the camera is often adapted to provide a magnification capability (as discussed elsewhere herein) such that images viewed through the camera are at least as magnified as if they were viewed through the devices described herein. Enhanced magnification is also often employed, to provide magnification levels beyond that which are typically utilized in an optical loupe. In certain frequent embodiments, detailed images are provided using electronic vision at the same magnification and quality as an intraoral camera or an extra oral camera.

The focal length is provided or adjustable in a manner that permits or requires the user to assume a predetermined vertical and horizontal distance from a known work area, and which predetermined vertical and horizontal distance from the known work area correlates with an ergonomically correct or appropriate posture for the user. This correlation, for example, refers to if the device is worn on the head of the user, proper viewing of the work are is only provided if the user assumes a predetermined ergonomic position.

In certain embodiments, the electronic vision option is provided with an adjustable focal length such that the camera can provided focused images of a work area if the focal length varies within a pre-defined distance. Such embodiments provide an important utility such that a desired focal length need not be built into the device, but rather is provided in an adjustable manner. In related embodiments, the angulation of the camera or vision through the camera, and/or the corresponding focal length, is/are adjustable to permit the user to assume multiple different (and desirably ergonomically correct) positions relative to a work area. This adjustment may be automatic or manual. Manual adjustment is often accomplished through manual adjustment of a direction of a camera or optical device such as a prism or mirror.

Automatic adjustment may be accomplished through, for example, the use of a tracking algorithm, software, or firmware that centers the line of sight regardless of the movement of the device or user wearing the device. Fiducials identifiable by the device or its operating code may be utilized to identify a portion, or boundaries, of a work area in the case of automated tracking to delineate a specific area for the camera to focus. In certain embodiments, the camera or tracking algorithm, software, or firmware controlling the camera is adapted with facial recognition capability such that the camera can recognize the location of a work area such as a mouth or other operation site of a subject. In the case of a medical procedure, anatomic reference points may be utilized to establish a specific area for the camera to focus, for example via automated tracking. Visual cues specific to the work area (e.g., page boundaries, surgical tools or equipment, dyes, colors, natural or synthetic patterns, bar codes, facial features, etc.), depending on the task or purpose for viewing the work area, will often be utilized to establish a specific area for the camera to focus, for example via automated tracking. In practice, though it may remain active, alternatively automated tracking may be utilized to permit the user to assume an ergonomically correct position to establish an optimal line of sight, and thereafter automated tracking may be turned off to lock the line of sight for the device in an optimal ergonomically correct position. Automated tracking may be activated or turned off by any of a variety known mechanical or electronic adaptations controllable by a user. Tracking such as automated tracking may also be provided in a timed manner such that once activated, it will automatically end upon the expiration of a predetermined time period to lock the line of sight after automated tracking ends.

The camera is often provided with auto-focus capability. Preferably, the auto focus capability permits fine focusing within small distances along the focal length to provide sharp images. For example, the camera is capable of auto focusing at any point along an exemplary focal length of between about 18 inches to about 48 inches. In certain embodiments, the focal length is between about 12 inches to about 60 inches. Most embodiments employ a localized focal length, but in certain embodiments (often in the media, entertainment, military, and hobbyist arenas) long range or telescopic focal lengths may often be desired. Often, such auto focus is fine auto focusing. Auto focus capabilities may be provided, for example, through known methodologies, such as those provided with MEMS capabilities in U.S. Patent App. Pub. Nos. 20140184890, 20140184881, and 20140184899.

In certain embodiments automated tracking is not utilized and the angulation and/or focal length is manually adjusted by the user. Magnification strength is often also provided in a manner that is adjustable by the user through any of a variety of mechanisms, including foot or hand operated mechanisms. In certain embodiments, control over one or more functions of the camera such as magnification strength, focal length, angulation, etc., is/are controlled using a hand-held device such as a dentist mirror or probe held by the user. In certain frequent embodiments, such controls are provided through voice commands or prompts.

In certain embodiments, when voice-control is provided over any or all functionality of the devices described herein, a microphone or voice/sound-recognition modality is included to ensure the device responds to appropriate prompts. For example, a microphone in certain embodiments is attached to the device and positioned, or movable to, within close proximity of the mouth of the user. In certain embodiments, the microphone is built into the housing of the device. Also in certain embodiments, the microphone is connected with the device controls or operating system via wireless connection (e.g., WPAN/Bluetooth, Coexistence, High Rate WPAN, Low Rate WPAN, mesh Networking, Body Area Networks, WiFi, WiMax, other wireless networks, Visible Light Communication, etc.).

As noted, the present device is operable with the same or similar functionality as an intraoral camera. Optical and/or digital zoom technologies coupled with dental office data connectivity often provide such functionality. While the present device is not intended to be inserted within the mouth of a subject, similar or equivalent images to an intraoral camera, which are well-known in the dental arts, are capable of being obtained. For example, in certain embodiments indirect images are captured of a work area. The present device provides magnification levels equivalent with that of present intraoral cameras. Indirect images may be obtained, for example, by imaging a work area reflected from a mirror such as a surgical, dental, or dentist's mirror. In such embodiments, an image of the work area is captured by focusing the camera on the mirror that is reflecting an image of the work area.

As also noted, the present device is operable with the same or similar functionality as an extra oral camera. Optical and/or digital zoom technologies coupled with dental office data connectivity often provide such functionality.

In most embodiments, the device can be equipped with on-board or connected touchpad or on-board swipe-pad control, for example, similar to the control of the Epson Moverio™ or Google Glass™ glasses.

The camera is generally provided in data connectivity with imaging software. For example, in certain embodiments the camera is integrated with an imaging software systems similar to, or such as, DEXIS, Eaglesoft, XDR, Apteryx, MiPACS, Tiger View, MacPractice, Carestream, Prof Suni, VixWin, Kodak, Romexis, and/or Schick. In other embodiments, the camera is integrated with another imaging software program. Imaging for general dentistry, orthodontics, Caries detection, cosmetic work, oral and maxillofacial surgery, among other purposes is contemplated. Imaging software is often utilized to aid diagnosis, obtain procedure approval, educate patients, educate students, design treatment protocols, guide treatment, validate protocols, develop new modalities, etc.

In general, a computer system necessary to process image information comprises is included comprising, for example, a CPU, Network Interface, display device, high speed display device I/F board, Input device I/F, GPU, Media Reader, Memory, Component, Hard drive I/F and Hard Drive, High performance cooling unit, Wireless or Network I/F, Bundled Software, and operating system.

In certain embodiments, image processing and display can be done on a work station or tablet processor (with 2D or 3D capability) with appropriate specifications. Exemplary specifications often include a High Resolution (Touch) Screen with Naked Eye or glasses enhanced 3D, Dual Core Cortex, Wi-Fi, Android or iOS OS, 1 GB RAM or greater, and at least 8 GB Internal Memory. With 3D engine chips, 3D image intertwined decoding and a switchable parallax barrier LCD screen can be provided to achieve the 3D stereoscopic video without glasses, supporting the exemplary video formats, 2D Video: MPEG 1/2/4, H.264, MJPEG, VC1, WMV, Real Video format video, 1080P resolution, 4K resolution, Photo formats can be supported with, for example: BMP, JPG, JPEG and other known formats; 3D Images can be supported with, for example: MPO-3D image format.

In certain embodiments, the software environment bundle often includes an operating system (OS), 2D or 3D custom proprietary display drivers, 2D or 3D camera, 2D or 3D multiplexed video player, 2D or 3D processor graphical user interface (GUI) menu driven control system, (dual) Universal Serial Bus (USB-2.0-3.0) input line 2D or 3D, single USB input stereo pair (USB 2.0-3.0) line 2D or 3D, Direct or Open GL CAD visualization line 2D or 3D, web conferencing 2D or 3D, CAD visualization 2D or 3D, 3D CAD file format converter, 2D or 3D stereoscopic raw uncompressed alternating, 2D or 3D stereoscopic raw uncompressed over and under switchable format, 2D or 3D stereoscopic raw uncompressed side-by-side switchable format, bundled software executable's are often preinstalled, and 2D or 3D dual camera multiplexed wire or wireless channel.

As indicated, in the most frequent embodiments, the device is worn by a user as would be a pair of spectacles. Alternatively, the display is provided in a visor portion. The display is presented in front of the eyes of the user as would be the lenses of such spectacles. The image displayed, for example, inside or adjacent to the lens or frame of the spectacles. Stereo displays and a mono displays are contemplated. Displays contemplated herein are therefore near-view displays. Near-view displays contemplated herein provide, for example, equivalent visual acuity in images displayed close to the eyes as they would be if viewed from a slight distance. An exemplary display technologies are provided, for example, in PCT Publication Nos. 2015095737, 2015048911; U.S. Patent App. Pub. Nos. 20150022542, 20140132484, 20130235331, 2013044042, US20120235887, US20120119978, the contents of each of which are incorporated by reference. Further examples of screen types are provided elsewhere herein. In other embodiments, a screen such as an LCD screen, plasma, prism-reflective, or projector screen may be provided adjacent to, as part of, or forming, the display.

The wearable device is provided with a display for images captured by an on-board camera. This display is, in the most frequent embodiments, a see-through display such that the user can see through the display when it is not actuated or prompted to display images captured by the on-board camera or images fed from another source. When the display is prompted to display images from the camera the user views the images instead of, or in addition to, being able to see through the display. Often images are provided on a viewing area of the display.

In certain frequent embodiments images are displayed or projected on a display that is changeable from clear to opaque. Smart glass technologies such as electrochromic smart glass, photochromic smart glass, suspended particle smart glass, liquid crystal smart glass (e.g., polymer dispersed liquid crystal), nano smart glass, etc., device technologies are contemplated. The smart glass technologies are embedded in a portion of the display or provided in a film applied to the display. Electrochromic device technology, for example, typically comprises a multilayer stack including an electrochromic material, an ion conductor to permit ions to move in and out of the electrochromic material to cause the optical property change, and transparent conductor layers (e.g., transparent conducting oxides), over which an electrical potential is applied. Generally, when applied to the display, smart glass films are applied with optically clear adhesive available, for example, from Minnesota Mining & Mfg., Saint Paul, Minn. For smart glass technologies requiring an electric charge or signal to switch from clear to opaque, or vice versa, power to impart the electric signal (e.g., electric potential or charge) is provided from a battery on the device or another on-board or remote power source. In the most frequent embodiments, a smart glass technology is utilized that requires a signal (e.g., electric signal, magnetic signal/force, etc.) to switch from opaque to clear, and vice versa; but not to maintain the state of clear or opaque once either state has been achieved.

In such embodiments, the screen is frequently positioned in the line of sight of the user as would the lenses of a pair of spectacles. When the camera or imaging modality is not being utilized, the user can view directly through the screen as if it was a clear spectacle lens. The screen in such embodiments is queued in a manual or automated manner to transition from transparent to opaque, and vice-versa, such that in the opaque mode, a limited amount of light is permitted through the screen.

In the opaque mode often 50% or less (e.g., less than 30%, less than 20%, less than 10%, less than 5%, or 0%) of light rays are permitted to pass though the screen to the eyes of the user. In certain frequent embodiments, when "opaque" the display is shaded in coloration, for example as in a shade coloration in a pair of sunglasses. In such embodiments, the device is often adapted to wrap around the eyes of the user to provide light shielding from the sides, top, and bottom, in addition to within the line of sight to provide a dark environment for the user to view images projected or displayed on the screen. Shields or light barriers may be utilized to wrap around the areas peripheral to the line of sight of the user such as the top, sides, and/or bottom areas relative to the line of sight. Such shields or light barriers may be discreet portions of the device, part of the device housing or frame, or otherwise build into the device. Such embodiments permit the user to be able to switch between modes of using manual sight and electronic vision. The side, bottom, and/or top shields or light barriers may be provided with the same or similar material to the screen such that they all transition together or separately between transparent or opaque; or one or more of the side, top, and bottom shields or barriers are provided with opaque material that prohibits light entry. In operation, when the screen is transparent, the user can view a work area directly; and when the screen is opaque an image of the work area provided by an electronic vision option (e.g., a camera) is displayed or projected on the screen internal to the user's eyes such that the user can view the image on the screen in real-time, time-delayed, or fast-forward manner.

In certain embodiments, the display is movable into and out of the line of sight of the user. In such embodiments, when the display is outside of the line of sight of the user, the user can view the work area directly. And, when the display is positioned in the line of sight of the user, images from the camera are displayed or projected on the display. In such embodiments the display may be opaque or transition between transparent and opaque.

In certain embodiments, a shade is provided movably connected with the device. Such a shade is movable between a position that permits outside light to pass through to the eyes of the user, and a position that blocks all or a portion of the outside light from the user's eyes. For example, the shade may cover the outside portion of the display (110) in one position and not cover the outside portion of the display (110) in a second position. Exemplary shades may also cover peripheral portions of the device around the eyes of the user to limit the entrance of outside to the user's eyes.

Limiting outside light from contacting the user's eyes is often advantageous when the display is operating to enhance visual acuity of images displayed or projected on the display.

In certain embodiments, the display is not a see-through display, but direct vision of the user is nonetheless provided while wearing the device containing the display. Often, in such embodiments, a dedicated camera is provided in a face-forward orientation (e.g., a face-forward camera). The face-forward camera may include a wide-angle or wide-aperture lens, or another lens, to mimic normal sight of the user. In operation, then the user would like to switch from viewing the work area to direct vision, the device is actuated to switch from displaying images from the work area viewing camera to displaying images from the face-forward camera.

In certain embodiments, an apparatus described herein includes one or more of a variety of electronic vision options. In certain embodiments, a camera (preferably a high-definition camera) is focused through the line of sight of the apparatus. This camera, for example, is capable of taking still images or video capture. The operation of the camera in such embodiments often involves line of sight angulation and magnification as described herein. Alternatively, the camera can be provided in an angle that does not require line of sight angulation, but permits the user to assume an ergonomically correct or appropriate posture when viewing a work area. In such embodiments, the camera is often adapted to have a predetermined focal length, which is often adjustable. Also, in such embodiments, the camera is often adapted to provide a magnification capability such that images viewed through the camera are at least as magnified as if they were viewed through the improved loupes or add-on device described herein. Often, in such embodiments, the focal length is provided in a manner that requires the user to assume a predetermined vertical and horizontal distance from a known work area, and which predetermined vertical and horizontal distance from the known work area correlates with an ergonomically correct or appropriate posture for the user. This correlation, for example, refers to if the device is worn on the head of the user, proper viewing of the work area is only provided if the user assumes a predetermined ergonomic position.

In electronic vision embodiments, the apparatus may be provided with a viewing area (display) for images captured by the camera. Often the viewing area (display) is a screen displaying or projecting images captured by the camera. Often, the screen is worn by the user as would be a pair of spectacles, with the image displayed inside or adjacent to the lens or frame of the spectacles. In certain embodiments, the display is present in a visor portion. Frequently, a screen such as an LCD screen, plasma, or projector screen is provided adjacent to, as part of, or forming, a front shield. For example, the image may be displayed on at least a portion of the front shield of the device. A variety of types of displays are contemplated, for example, those described in U.S. Patent App. Pub. Nos. 20130235331, 20080169998, 20100110368, 2013044042; and U.S. Pat. Nos. 6,023,372 and 8,744,113, though including adaptations described for such displays described herein.

In certain embodiments, the electronic vision mechanism provides functionality for the user to view or detect photo-activated or chemically activated substances in real-time such as a radiolabel, a fluorophore or fluorescent dye, biotin, an enzyme, a chemiluminescent compound, or another type of detectable signal. This can be used, for example, to help detect carious lesions on the tooth structure to make sure the tooth has been adequately debrided. The electronic vision option also provides, in certain embodiments, infrared imaging capability. In certain embodiments, the electronic vision mechanism incorporates a fluorometer or luminometer. In such embodiments, the electronic vision mechanism may be provided in a manner that it can distinguish emission light within certain wavelengths, for example emissions provided by the following exemplary fluorescent dyes: rhodamine dyes tetramethyl-6-rhodamine, and tetrapropano-6-carboxy-rhodamine, and the fluorescein dyes 6-carboxyfluorescein and, each in combination with a DABCYL quencher. Other suitable dyes include, for example, 5'-hexachlorofluorescein phosphoramidite, and 2',7'-dimethoxy-4',5'-dichloro-6-carboxyfluorescein, BIOSEARCH BLUE® (BG5-5088), CAL FLUOR® Gold 540, CAL FLUOR® Orange 560, CAL FLUOR® Red 590, CAL FLUOR® Red 610, CAL FLUOR® Red 635, PULSAR® 650, Quasar 670, Quasar 705, among others. Often, in such embodiments, the device incorporates a proper excitation signal source such as an LED that emits a light signal within the excitation spectrum of the photoactivated substance, in addition to appropriate filters and optics. Such embodiments may employ a camera such as a CMOS camera (e.g., IDS UI-5490HE) or a CCD camera (e.g., Lumenera LW11059 or the Allied GE4900) to detect emission signals.

In certain embodiments, the presently described device is capable of taking and analyzing an image in a work area in addition to and an image of the eyes of a user to provide information about the work area (or object within the work area) selected by the gaze of a user based on the result of an analysis. See, e.g., U.S. Patent App. Pub. No. 20150002676. In certain related embodiments, the presently described device is capable of executing a specific function corresponding to a gesture of an eye, or eyes, of the user based on the result of the analysis. See id. Imaging of the eyes of the user often provides enhanced functionality to the present devices for controlling functions of the device camera (e.g., camera direction, imaging modality, or focus), display (e.g., viewing images from a camera or another source, operation of smart glass functionality, etc.), or other data-connected connected functions contemplated herein.

In frequent embodiments, the present system is compatible with implant imaging software. Generally, such compatibility involves integration such that real-time images during implantation are provided on the display to the user. Implant imaging systems that provide implant imaging such as visualization of the work area and any dental tools utilized to perform implantation, including angulation, location, and movements thereof are similarly provided on the display. Often, such imaging is derived from a device other than the camera on-board the device (e.g., external sensors or imaging modality) and images are fed to the display through an external input and provided via corded or wireless data (e.g., WPAN/Bluetooth, Coexistence, High Rate WPAN, Low Rate WPAN, mesh Networking, Body Area Networks, WiFi, WiMax, other wireless networks, Visible Light Communication, etc.) transmission.

The display also often accepts inputs that are useful for operating or managing a busy practice. For example, external messaging may be provided on the display for viewing by the user while the user is wearing the device. Such external messaging is often in the form of internal office messaging to enhance real-time communication within the office. For example, the front staff can communicate with the user information about patients in the office or expected patients in the office, information about timing and workflow, information about insurance and procedure approvals, or to provide messages to be relayed to others in the office including patients. A variety of other messaging options and capabilities are contemplated herein to provide real-time messaging to the user, for example during a procedure, such that verbal or audible distractions are obviated, for example, to preserve confidentiality. Such messaging functionality is also often provided in systems and devices utilized by non-medical arena users, such as users in the telecommunications or media areas, hobbyists, or lay people.

Remotely positioned imaging modalities and data sources in optical communication with the display are contemplated. The types and locations of the remotely positioned imaging modalities is non-limiting.

Using display functionality described herein, the user can obtain images of a procedure or of specific aspects of a work area that are useful or necessary to obtain approval for a medical procedure from an insurer or other approval source. The user is able to, for example, select specific images or videos and upload them to a billing or procedure approval system. As such, the presently described devices increase workflow to e-claims for insurance coverage. The device capabilities often provide a conjunctive aid in diagnosis. Such functionality aids workflow in an office and results in less time for procedures and the ability to see additional patients in a work day.

Other features and advantages of the disclosure will be apparent from the following detailed description, and from the claims. The present disclosure is provided using a variety of examples provided herein. The examples are provided solely to illustrate by reference to specific embodiments. These exemplifications, while illustrating certain specific aspects of the disclosure, do not portray the limitations or circumscribe the scope of the disclosure. Citation of the above publications or documents is not intended as an admission that any of the foregoing is pertinent prior art, nor does it constitute any admission as to the contents or date of these publications or documents.

We claim:

1. A wearable optical system, comprising:
   a user wearable frame comprising a display that is viewable by a user via a horizontal optical path, wherein a first frame support attaches the display to the user wearable frame; and
   a vision redirecting mechanism comprising a camera defining a work area optical path, wherein the camera is in optical communication with the display such that an image captured by the camera is transmitted to the display, the work area optical path being oriented downward relative to the horizontal optical path,
   wherein the vision redirecting mechanism is comprised in a cantilevered vision directing mechanism on an imaging extension comprised in the user wearable frame, wherein a second frame support attaches the imaging extension to the user wearable frame.

2. The system of claim 1, further comprising a light source configured to emit a light signal that is coextensive with the work area optical path.

3. The system of claim 1, wherein the display is comprised in a lens supported by the frame.

4. The system of claim 1, wherein the optical communication comprises data transmission of an image obtained by the camera to the display.

5. The system of claim 1, wherein the display comprises an inner surface and an outer surface and the outer surface comprises smart glass.

6. The system of claim 1, wherein the vision redirecting mechanism or display is in data communication with a laboratory information system, a medical apparatus, or an insurance efiling system.

7. The system of claim 1, wherein the work area optical path is oriented downward at an angle relative to the horizontal optical path.

8. The system of claim 7, wherein the angle is between 55° to 100°.

9. The system of claim 1, wherein the vision redirecting mechanism or the viewing portion magnifies an image passed through the work area optical path and the imaging magnification comprises between about 2.0× to 400.0× magnification of the image.

10. The system of claim 1, wherein the optical communication comprises direct image transmission across the work area optical path and horizontal optical path.

11. The system of claim 1, wherein the display is adapted to provide an image from a device or camera not physically connected to the device and positioned in a location that is remote relative to the device.

12. A wearable optical system, comprising:
    a user wearable frame;
    a centered display supported by the frame by a first frame support; and
    a cantilevered imaging modality comprised in an imaging extension supported by the frame by a second frame support in data connection with the display, wherein the first frame support and the second frame support are positioned at different locations on the frame.

13. The system of claim 12, wherein the frame comprises an eyeglass frame.

14. The system of claim 13, wherein the imaging modality comprises a camera.

15. The system of claim 14, wherein the imaging modality or display is adapted to be remote controlled by the user using a hand-held tool or device.

16. The system of claim 12, wherein the imaging modality is oriented between about 30° to about 100° below horizontal.

17. The system of claim 16, wherein the imaging modality or display is voice-controlled.

18. The system of claim 12, wherein the display comprises inner and outer portions, and the outer portion comprises smart glass.

19. The system of claim 12, wherein the display is adapted to provide an image from a device or camera not physically connected to the device and positioned in a location that is remote relative to the device.

20. A wearable optical system, comprising:
    a user wearable frame comprising a viewing portion comprising a display defining a horizontal optical path for the user, wherein the display comprises an inner surface and an outer surface and the outer surface comprises smart glass; and
    a vision redirecting mechanism comprising a camera that redirects the horizontal optical path to a second optical path defined by a different angle versus the horizontal optical path, wherein the vision redirecting mechanism magnifies an image passed through the second optical path and the horizontal optical path.

* * * * *